(12) United States Patent
Langan et al.

(10) Patent No.: US 8,382,717 B2
(45) Date of Patent: *Feb. 26, 2013

(54) SAFETY DEVICE FOR DRUG DELIVERY DEVICES AND CONTAINERS

(75) Inventors: Amy Elizabeth Langan, Chicago, IL (US); Richard John Kruzynski, Long Grove, IL (US); John Anton Kollar, III, Northbrook, IL (US); Patricia Lynn Miyake, Mundelein, IL (US); Monique LaSayre Kruk, Burlington, WI (US); Mark Francis Wagner, Gurnee, IL (US)

(73) Assignee: Pharmedium Services, LLC, Lake Forest, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/038,937

(22) Filed: Mar. 2, 2011

(65) Prior Publication Data

US 2011/0152834 A1 Jun. 23, 2011

Related U.S. Application Data

(63) Continuation of application No. 12/123,301, filed on May 19, 2008, now Pat. No. 7,918,830.

(60) Provisional application No. 60/991,994, filed on Dec. 3, 2007.

(51) Int. Cl.
*A61M 3/00* (2006.01)
(52) U.S. Cl. ............. 604/189; 604/404; 40/638; 283/81
(58) Field of Classification Search .................. 604/189; 283/81, 74, 75, 72
See application file for complete search history.

(56) References Cited

U.S. PATENT DOCUMENTS

| | | | |
|---|---|---|---|
| 3,287,839 A | 11/1966 | Rotwein et al. | |
| 4,065,343 A | 12/1977 | Stumpe | |
| 4,725,077 A | 2/1988 | Fujita | |
| 4,815,768 A | 3/1989 | Applebaum et al. | |
| D311,423 S | 10/1990 | DeSantis | |
| 5,426,520 A | 6/1995 | Kakae et al. | |
| D386,212 S | 11/1997 | Lambert | |
| 5,692,640 A | 12/1997 | Caulfield et al. | |
| 5,924,561 A | 7/1999 | Baumgartner et al. | |
| 6,089,611 A | 7/2000 | Blank | |
| D432,176 S | 10/2000 | Stevens et al. | |
| 6,299,213 B1 | 10/2001 | Souparis | |
| D453,529 S | 2/2002 | Roth | |
| 6,568,530 B2 | 5/2003 | Takahashi et al. | |
| 6,578,875 B2 | 6/2003 | Tamura et al. | |

(Continued)

OTHER PUBLICATIONS

Drug delivery device label for Phenylephrine, known prior to Dec. 3, 2007, 1 page.

(Continued)

*Primary Examiner* — Kevin C Sirmons
*Assistant Examiner* — Brandy C Scott
(74) *Attorney, Agent, or Firm* — K&L Gates LLP

(57) ABSTRACT

A drug administration safety device having a label configured to be attached to a drug container such as a syringe or IV bag, an adhesive on the back face of the label, and a backing or substrate for holding the label and protecting the adhesive prior to the application of the label to the drug container. In one embodiment, the label includes a first drug name section in a first orientation, a second drug name section in a second orientation, a third drug name section in a third orientation, a drug concentration section, a variable information section, and a gradiation viewing section. The first orientation, second orientation, and third orientation are different from each other to enable a user to readily see the drug name regardless of the position and orientation of the drug container.

16 Claims, 49 Drawing Sheets

U.S. PATENT DOCUMENTS

| | | | |
|---|---|---|---|
| 6,835,430 | B2 | 12/2004 | Morii et al. |
| D500,524 | S | 1/2005 | Stewart et al. |
| D522,065 | S | 5/2006 | Greenstein |
| D550,287 | S | 9/2007 | Smart et al. |
| 7,311,205 | B2 | 12/2007 | Adler et al. |
| 7,458,612 | B1 | 12/2008 | Bennett |
| D588,200 | S | 3/2009 | Langan et al. |
| 7,918,830 | B2 * | 4/2011 | Langan et al. ............ 604/189 |
| 2002/0017784 | A1 | 2/2002 | Merry et al. |
| 2002/0056989 | A1 | 5/2002 | Lewis-Leander |
| 2006/0163869 | A1 | 7/2006 | Adler et al. |
| 2007/0029788 | A1 | 2/2007 | Adler |
| 2007/0252378 | A1 | 11/2007 | Chambers |
| 2008/0188814 | A1 * | 8/2008 | Lavi-Loebl et al. ........ 604/189 |

OTHER PUBLICATIONS

IV bag label for 0.9% Sodium Chloride, known prior to Dec. 3, 2007, 1 page.
IV bag label for Fentanyl and Ropivacaine, known prior to Dec. 3, 2007, 1 page.
Label for alcohol preps, known prior to Dec. 3, 2007, 1 page.
Label for drug vial for 0.9% Sodium Chloride, known prior to Dec. 3, 2007, 1 page.
Label for drug vial for Phenylephrine, known prior to Dec. 3, 2007, 1 page.
Label for drug vial for Vecuronium Bromide, known prior to Dec. 3, 2007, 1 page.
PCT International Search Report and Written Opinion for PCT Application No. PCT/US08/83171, 10 pages.
Picture of Cefazolin vial label, which was publicly available prior to Dec. 3, 2007, 1 page.
Pictures of Baxter 70% Dextrose Bag label, which was publicly available prior to Dec. 3, 2007, 1 page.
Pictures of Baxter Morphine syringe label, which was publicly available prior to Dec. 3, 2007, 2 pages.
Pictures of BD Heparin syringe label, which was publicly available prior to Dec. 3, 2007, 3 pages.
Pictures of Excelsior Heparin syringe label, which was publicly available prior to Dec. 3, 2007, 3 pages.
Pictures of Hospira 50% Dextrose syringe label, which was publicly available prior to Dec. 3, 2007, 3 pages.
Pictures of Hospira Calcium Chloride prefilled syringe label, which was publicly available prior to Dec. 3, 2007, 3 pages.
Pictures of Hospira Ondansetron I-Secure syringe label, which was publicly available prior to Dec. 3, 2007, 3 pages.
Pictures of Hospira Sodium Bicarbonate Abboject syringe label, which was publicly available prior to Dec. 3, 2007, 3 pages.
Pictures of Kendall Heparin prefilled syringe label, which was publicly available prior to Dec. 3, 2007, 3 pages.
Pictures of Labetalol syringe label, which was publicly available prior to Dec. 3, 2007, 4 pages.
Pictures of Medefil Heparin syringe label, which was publicly available prior to Dec. 3, 2007, 3 pages.
Syringe label for Atropine sulfate, known prior to Dec. 3, 2007, 1 page.
Syringe label for Calcium Chloride, known prior to Dec. 3, 2007, 1 page.
Syringe label for Labetalol Hydrochloride, known prior to Dec. 3, 2007, 1 page.
Original Complaint—*Unique Pharmaceuticals, Ltd.* vs. *Pharmedium Services, LLC*, dated Mar. 26, 2012 on 5 pages.

* cited by examiner

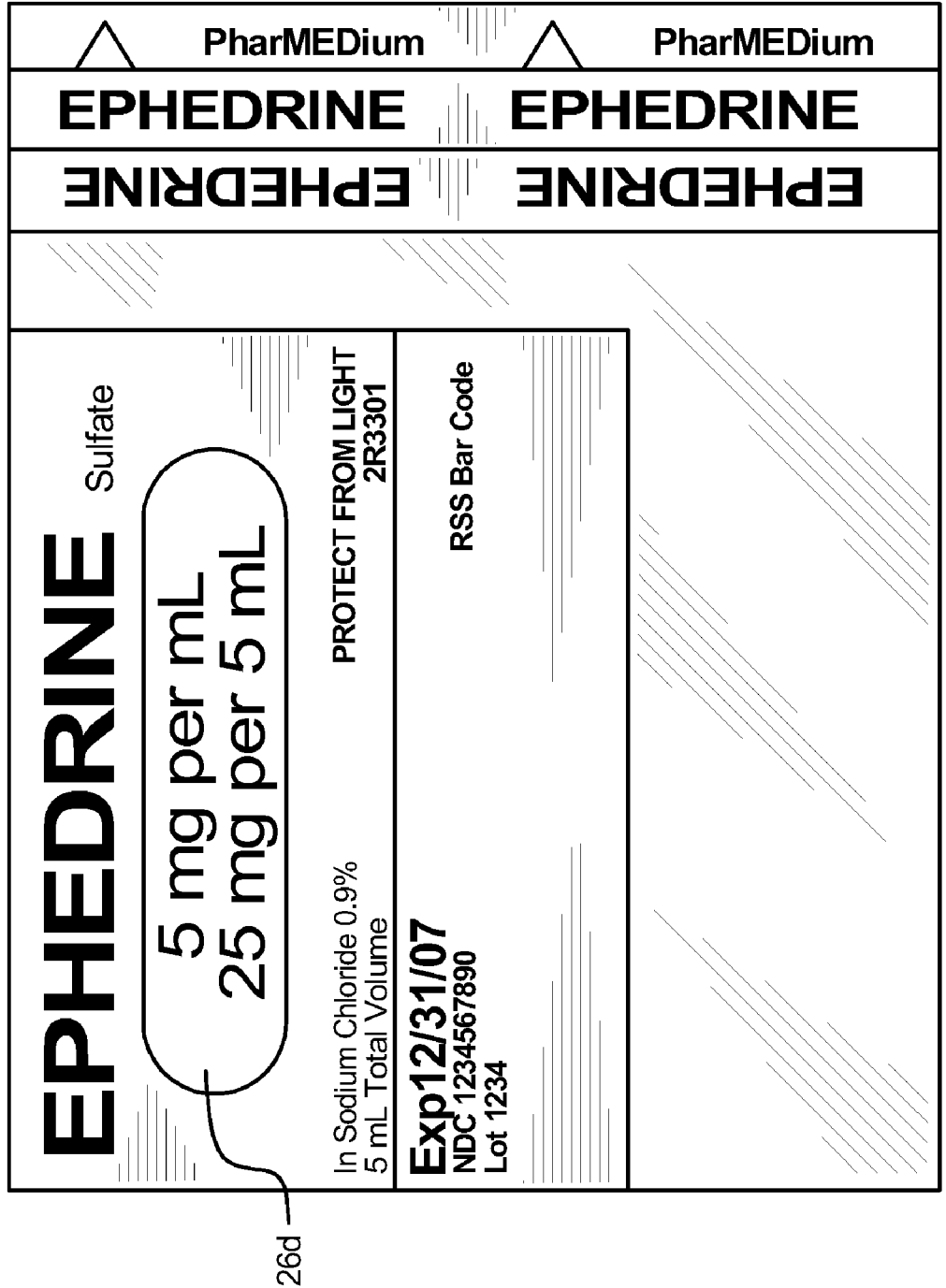

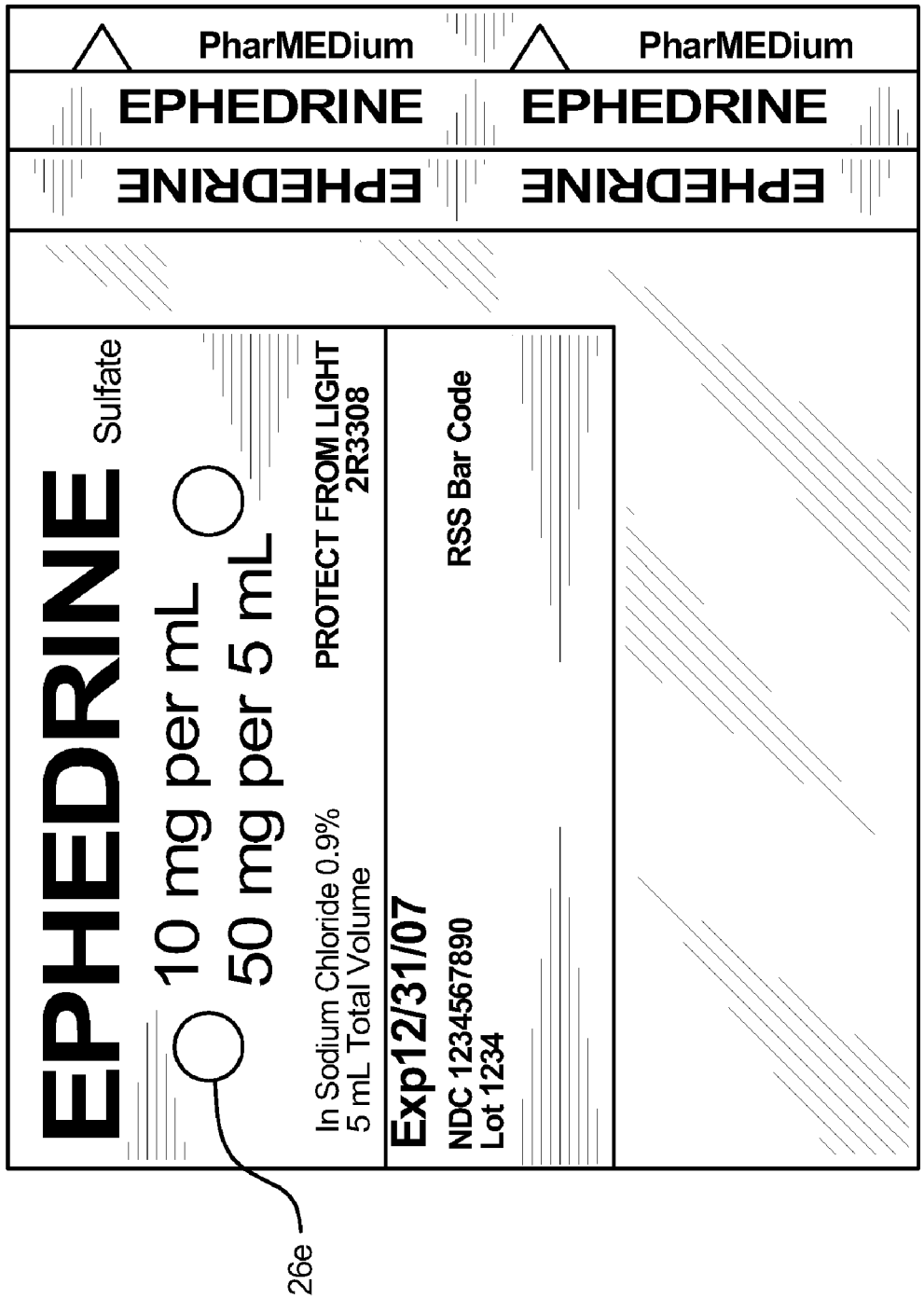

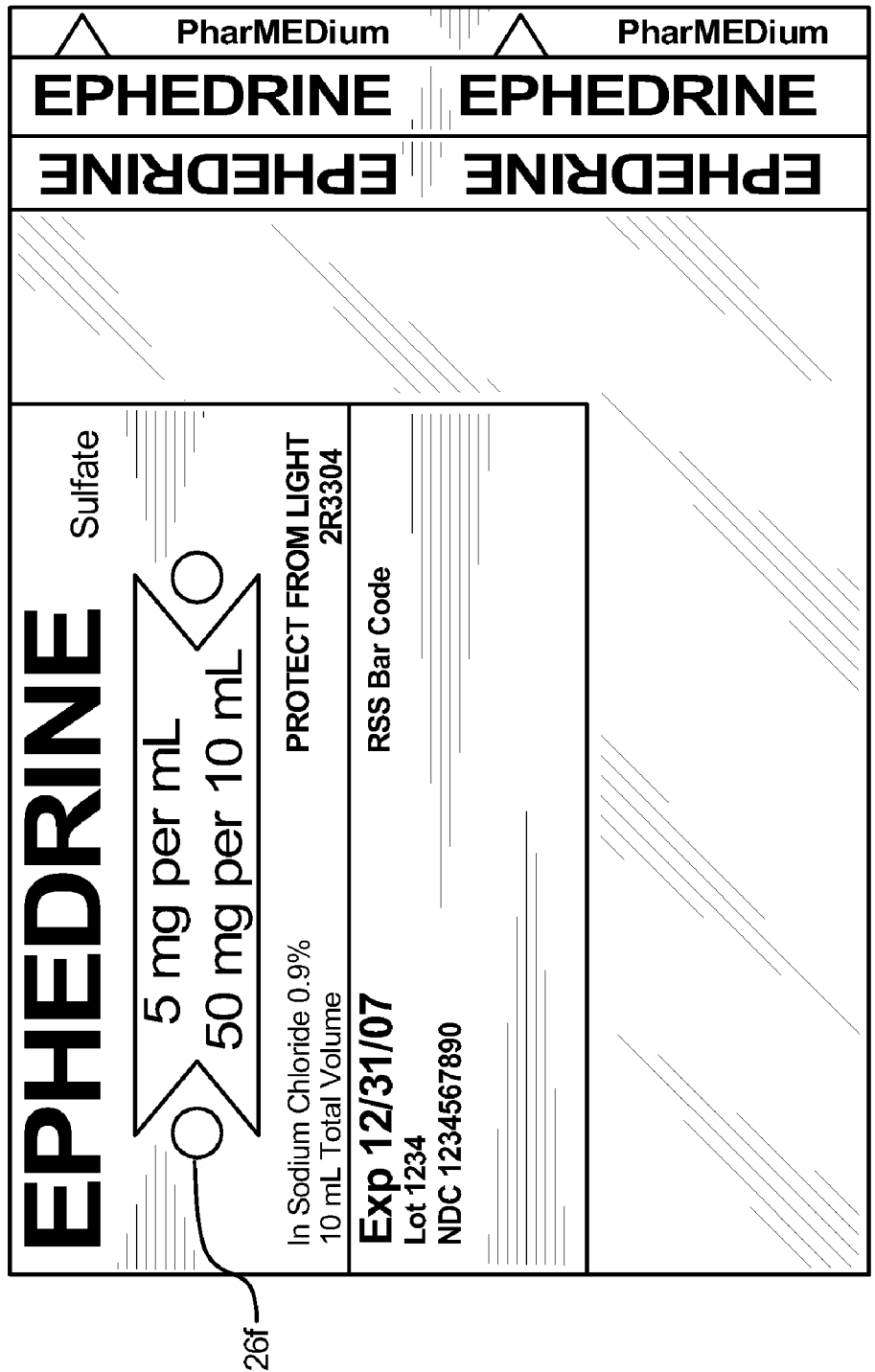

FIG. 2M

VECuronium Bromide
1mg per mL
10 mg per 10 mL
2R3302
In 0.9% Sodium Chloride
10 mL Total Volume
PROTECT FROM LIGHT
RT STORAGE VECuronium VECuronium PharMEDium
VECuronium VECuronium PharMEDium

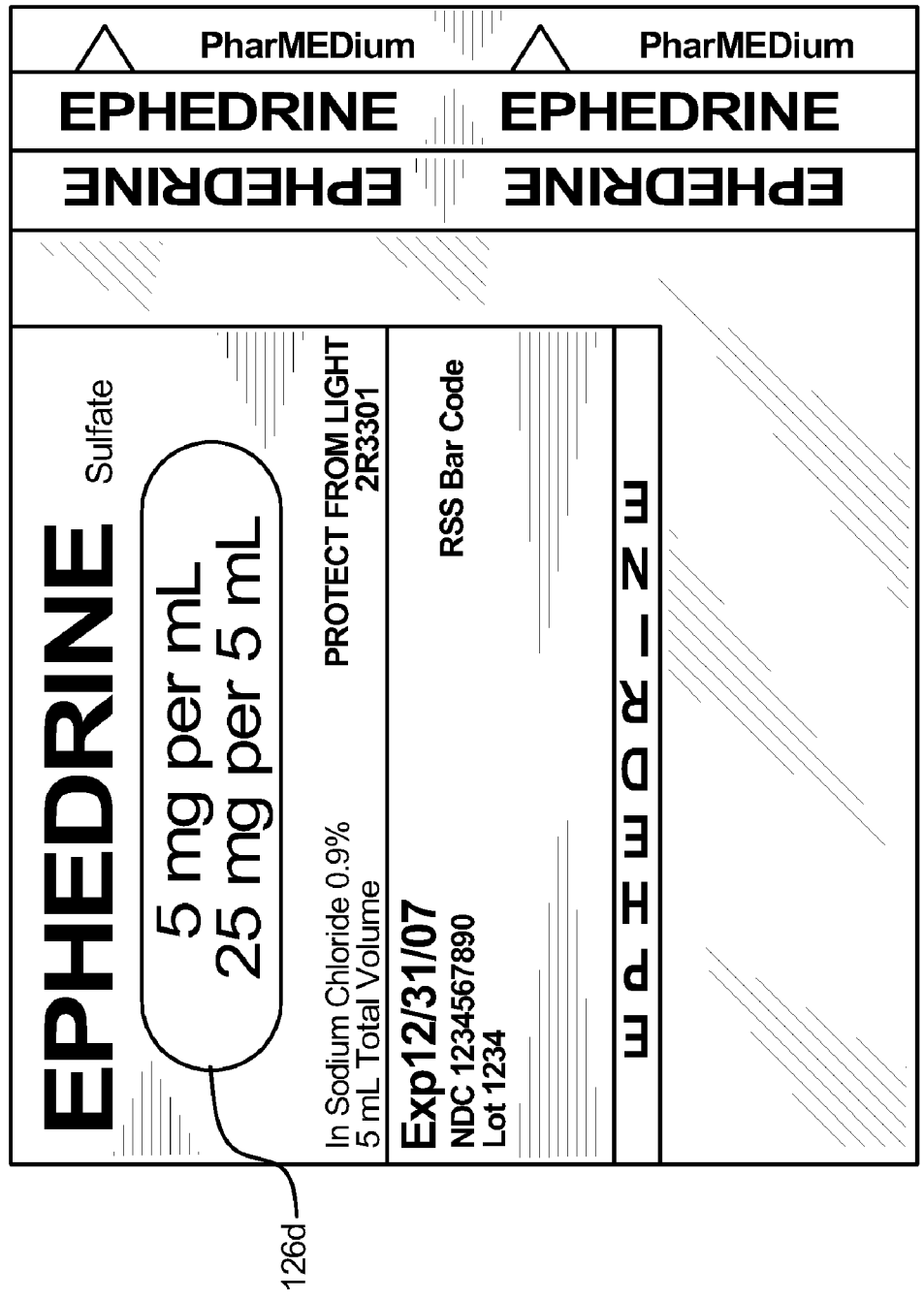

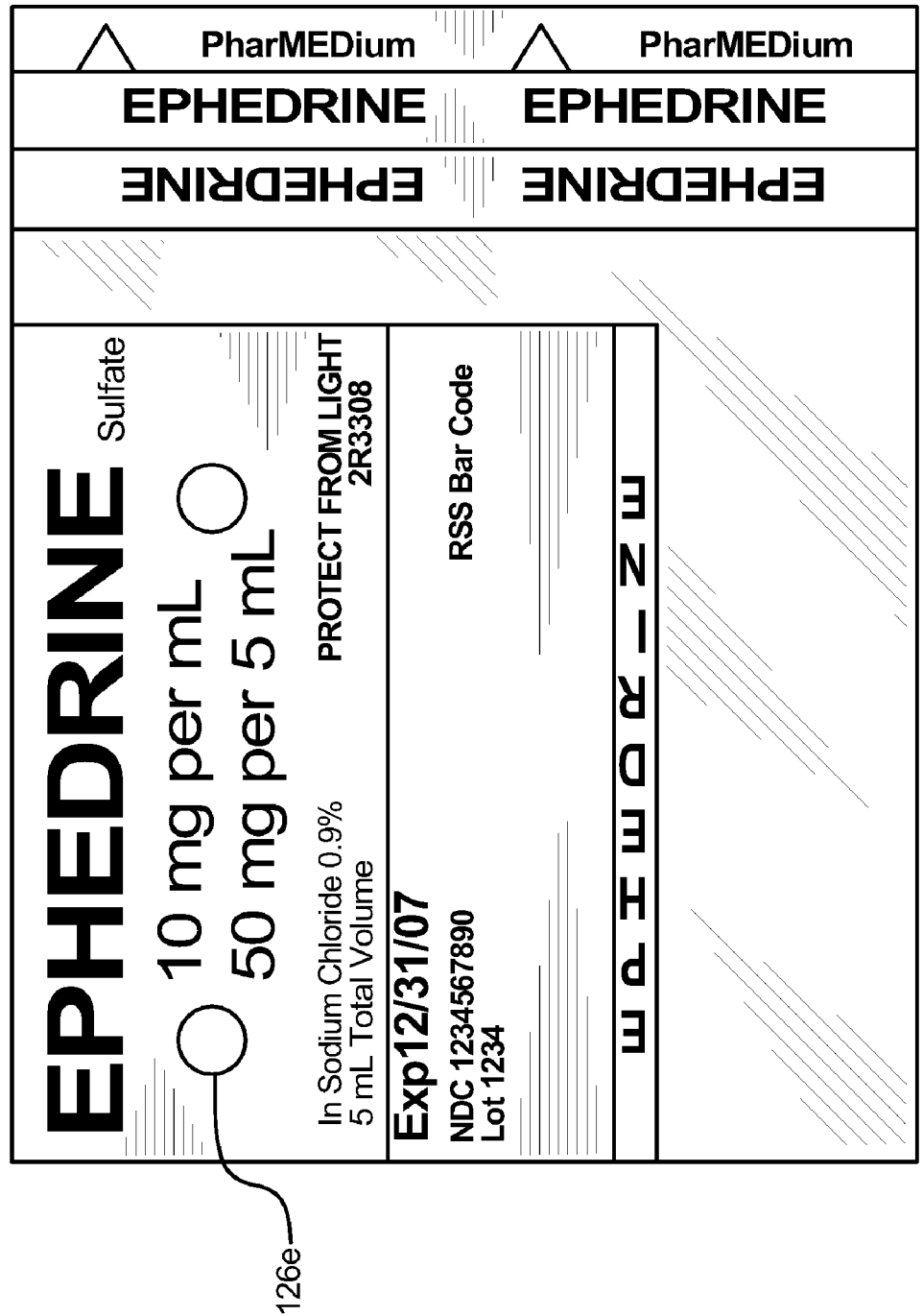

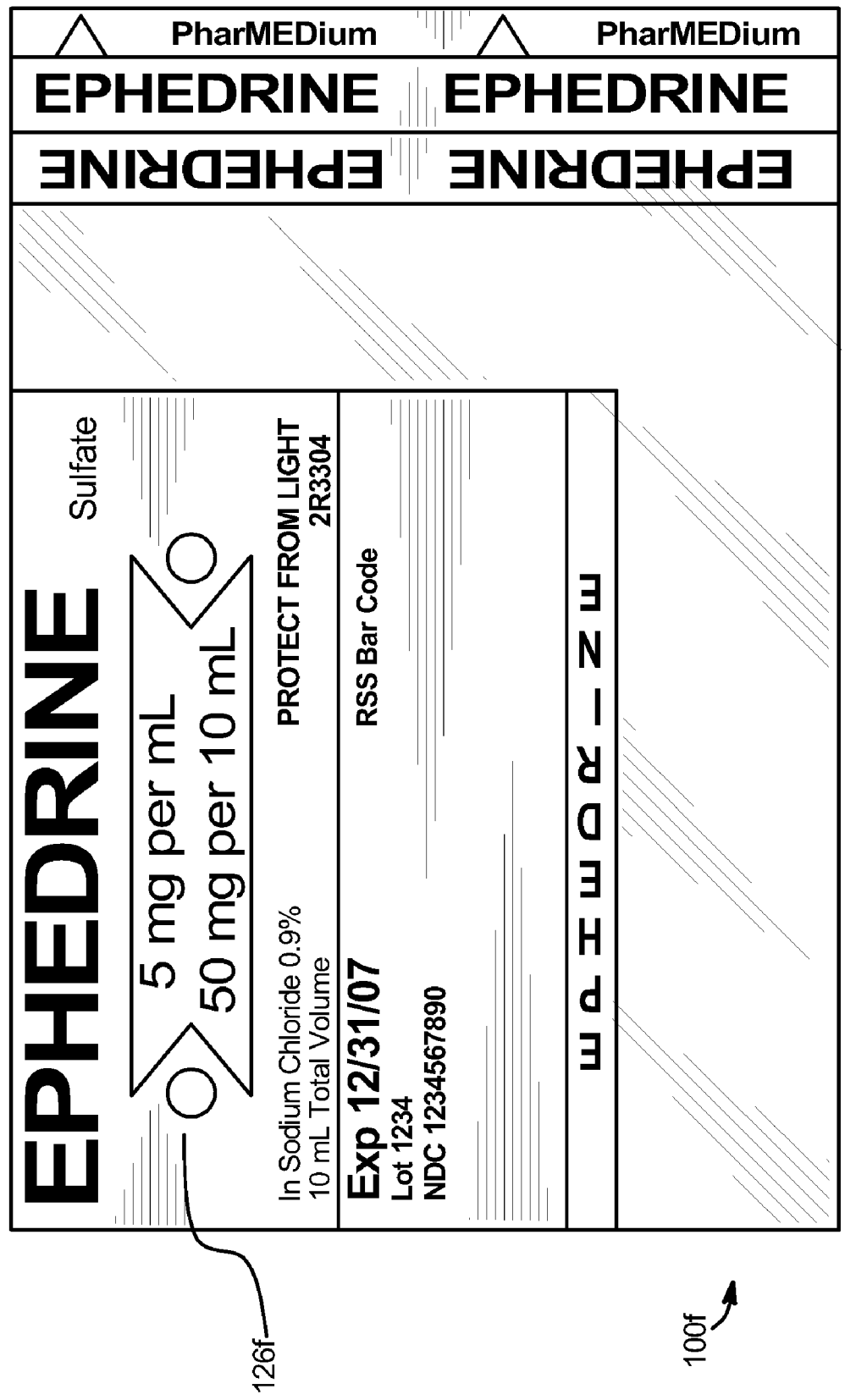

VECuronium Bromide
1mg per mL
10 mg per 10 mL  2R3302
In 0.9% Sodium Chloride   PROTECT FROM LIGHT
10 mL Total Volume   RT STORAGE

VECURONIUM

VECuronium  VECuronium  PharMEDium
VECuronium  VECuronium  PharMEDium

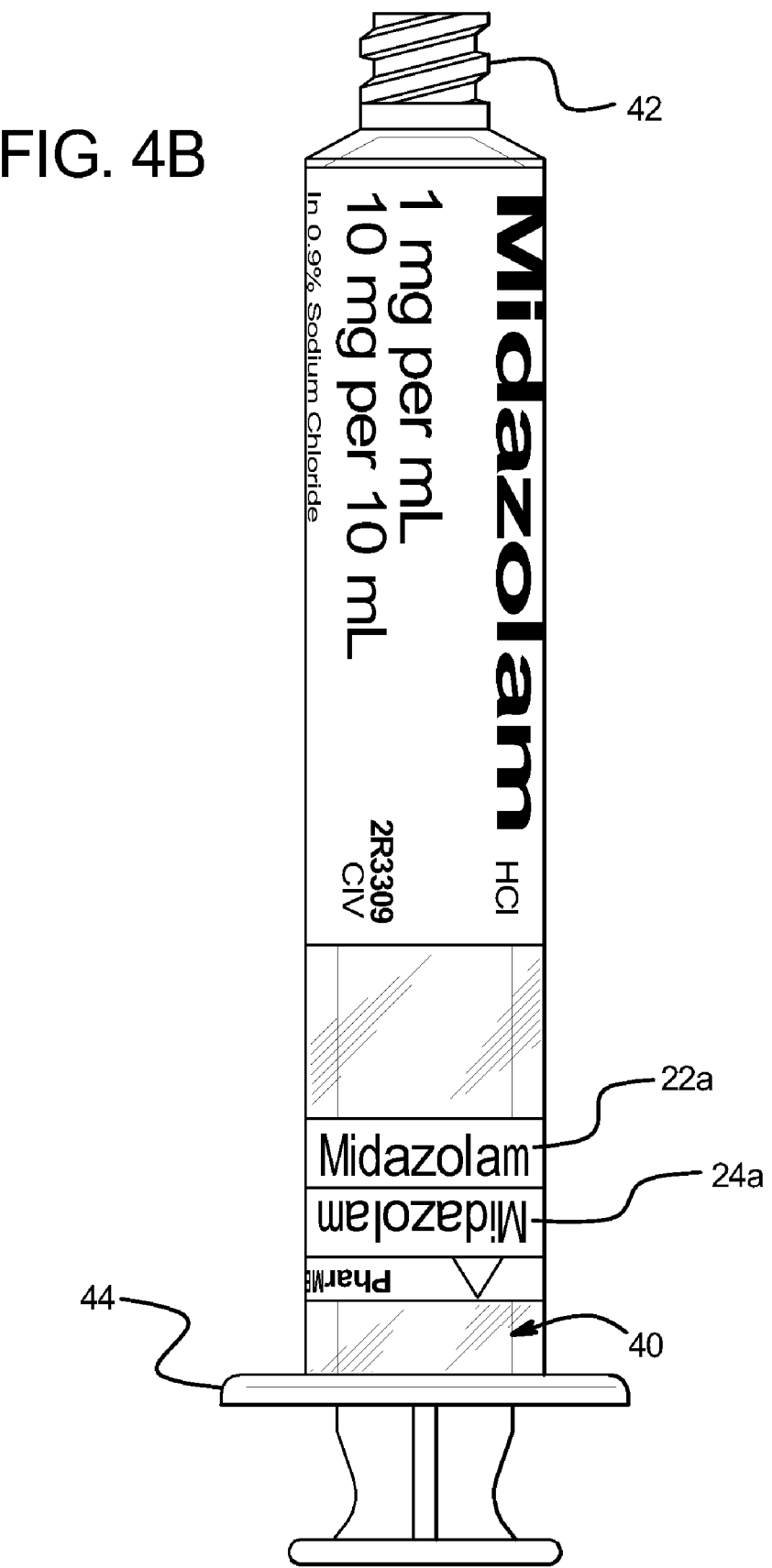

US 8,382,717 B2

SAFETY DEVICE FOR DRUG DELIVERY DEVICES AND CONTAINERS

PRIORITY CLAIM

This continuation patent application claims priority to and the benefit of U.S. patent application Ser. No. 12/123,301, filed May 19, 2008, which is a non-provisional patent application which claims priority to and the benefit of U.S. Patent Application No. 60/991,994, filed Dec. 3, 2007, the entire contents of which are incorporated herein by reference.

COPYRIGHT NOTICE

A portion of the disclosure of this patent document contains or may contain material which is subject to copyright protection. The copyright owner has no objection to the photocopy reproduction by anyone of the patent document or the patent disclosure in exactly the form it appears in the Patent and Trademark Office patent file or records, but otherwise reserves all copyright rights whatsoever.

BACKGROUND

According to the Institute of Medicine (IOM), medication or pharmaceutical errors harm at least 1.5 million people every year in the United States alone. The IOM further reports that at least one medication error per patient per day has occurred in each hospital in the United States during the 2006-2007 timeframe.

More specifically, if a drug is not promptly administered and delivered to a patient to correct a deviation from normal physiological parameters, a series of abnormal functions by the patient's body may result. For example, a patient under anesthesia during surgery may require prompt intervention to maintain certain systems and functions of the patient's body such as blood pressure, fluid balance and the like. An anesthesiologist or certified registered nurse anesthetist often must quickly use drugs at various different concentrations to counteract the stress on these systems and functions due to the surgery.

To administer and deliver a drug quickly to a patient, health care providers use routes of administration such as intravenous (IV) access to deliver drugs in liquid form to the patient. Many drugs are formulated to be administered by pump, IV container or by syringe and are pre-filled into these drug devices or containers for administration. A drug in the device or container is also formulated at a predetermined concentration to enable a suitable dose of the drug to be delivered in an appropriate volume, thereby eliminating the need for recalculating the dose or diluting the drug prior to its administration or between administrations. When using pre-filled syringes, for example, each containing a predetermined concentration of the drug for quick delivery of a drug to a patient, a health care provider (such as an anesthesiologist) must have readily available multiple similar syringes for multiple drugs and multiple similar syringes of different concentrations of the same drug. This may increase the likelihood of medication errors.

Certain steps have been taken to attempt to minimize errors in the administration of medications. For example, the American Society for Testing and Materials (ASTM) has established color schemes for labels to distinguish drug classes from one another. However, errors in administration of such drugs and medication to patients continue to persist. There is therefore a need for improved devices which further minimize drug or medication administration errors.

SUMMARY

The present disclosure provides various embodiments for a drug administration safety device which includes a label configured to be attached to a drug container such as a syringe or IV bag, an adhesive on the back face of the label, and a backing or substrate for holding the label and protecting the adhesive prior to the application of the label to the drug container. In various embodiments, the label includes multiple sections. In one embodiment, the label includes a first drug name section in a first orientation, a second drug name section in a second orientation, a third drug name section in a third orientation, a drug concentration section, a variable information section, and a graduation viewing section. The first orientation, second orientation, and third orientation are different from each other to enable a user to readily see (in an upright readable position) the drug name regardless of the position and orientation of the drug container. In a further embodiment, the label includes a fourth drug name section in a fourth orientation, which is also different from the first, second and third orientations. The present disclosure also provides a drug container having the label attached to the drug container by the adhesive.

In further embodiments, each label for a specific drug concentration section includes one or more specific shapes associated with such concentration. Thus, different labels for different concentrations of the same drug will have different shapes in the respective drug concentration sections of the different labels.

The present disclosure also provides various embodiments for developing schemes for differentiating labels for different concentrations of the same drug. In an embodiment, each of a sequence of different shapes is associated with each of the different concentrations of the same drug. The shape corresponding to the concentration to be included on a label for that drug is used in the drug concentration sections of the label for that drug.

An advantage of the present disclosure includes providing a drug administration safety device that reduces the risk of errors in administration of medication by presenting certain information in the label in various orientations to enable the user to readily read or recognize the information regardless of the position of the drug container.

Another advantage of the present disclosure includes providing a drug administration safety device that reduces errors in administration of medication by distinguishing similar drug containers for the same drug through the use of different visual cues such as different shapes associated with different concentrations of the drug.

A further advantage of the present disclosure is the creation of a systematic way of distinguishing different doses of the same drug through a sequence of different shapes associated with a sequence of increased doses of the drug and using the same or similar sequence of shapes associated with a sequence of increased doses of another drug.

Additional features and advantages are described herein, and will be apparent from the following Detailed Description and the figures.

BRIEF DESCRIPTION OF THE FIGURES

FIGS. 2A, 2B, 2C, 2D, 2E, 2F, 2G, 2H, 2I, 2J, 2K, 2L and 2M are plan views of drug administration safety devices of various embodiments of the present disclosure;

FIGS. 3A, 3B, 3C, 3D, 3E, 3F, 3G, 3H, 3I, 3J, 3K, 3L and 3M are plan views of drug administration safety devices of various embodiments of the present disclosure;

FIGS. 4A, 4B, and 4C are perspective views of an embodiment of the label of the drug administration safety device affixed to a syringe, each figure having the syringe oriented in a different position;

DETAILED DESCRIPTION

The present disclosure relates in general to apparatus and methods for making drug delivery devices or containers safer. The present disclosure describes various embodiments of drug administration safety devices for a drug delivery device or drug container such as a syringe or intravenous bag, and methods of clearly enabling users to readily differentiate different drug containers having different drugs or different concentrations of drugs in fast and reliable manner to minimize the chances of drug administration errors and potential harm to patients resulting therefrom.

Figure 4A:
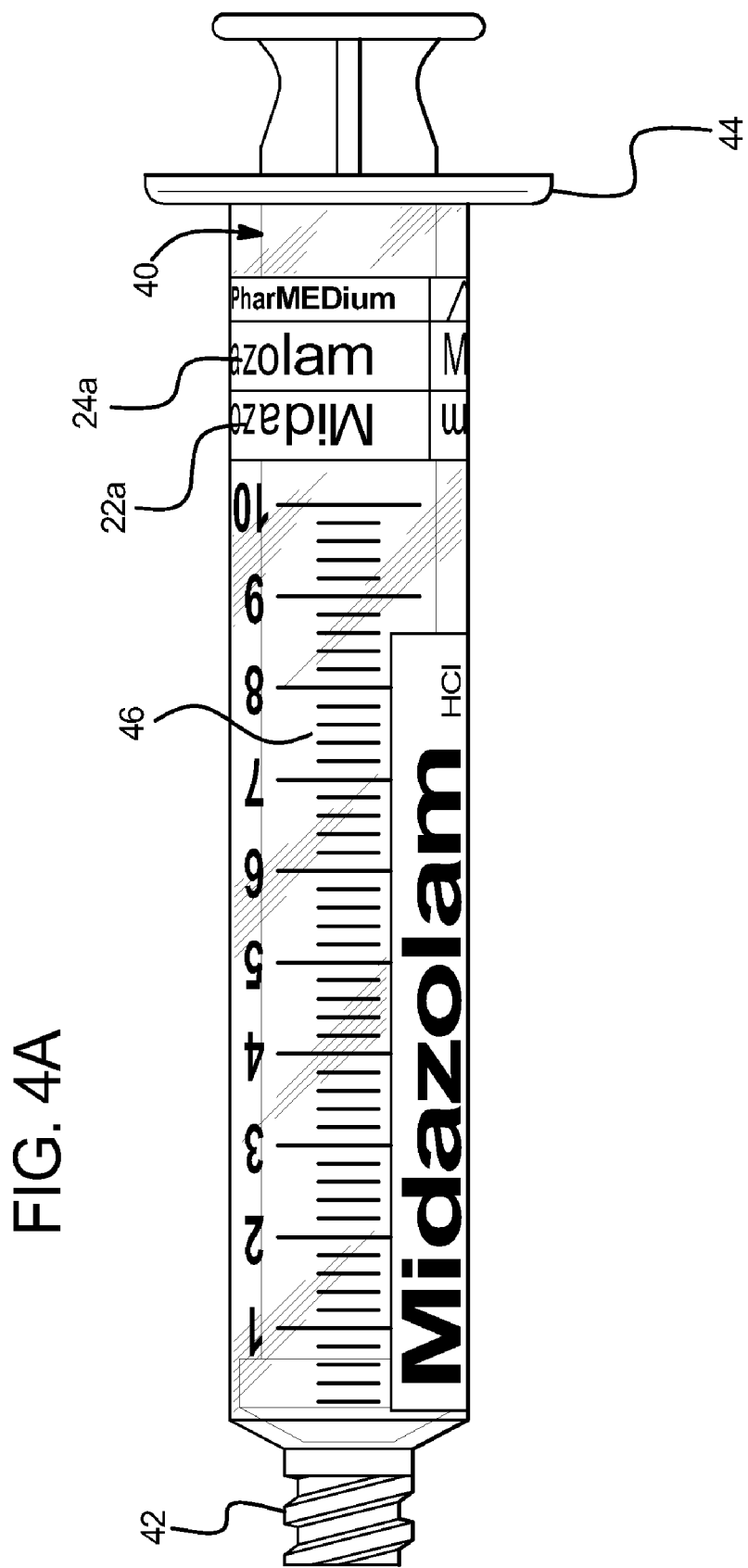
Figure 4C:
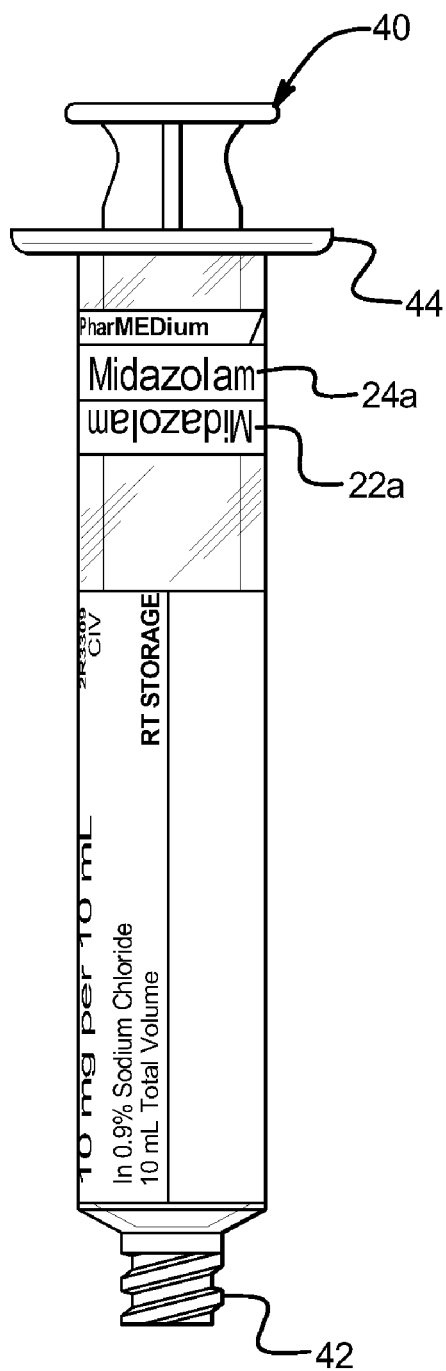

Referring now to the Figures, FIG. 1, FIGS. 2A, 4A, 4B, 4C, and 5 illustrate one embodiment of the drug administration safety device of the present disclosure, generally indicated by numeral 10a. The drug administration safety device 10a includes a rectangular label 12a configured to be attached to a drug container such as a syringe (i.e., wrapped around the syringe). For example, FIGS. 4A, 4B and 4C show label 12a removed from the backing 16 and positioned on a syringe 40. The drug administration safety device 10a also includes an adhesive 14 on the back face of the label 12a, and a backing or substrate 16 for holding the label and protecting the adhesive prior to the application of the label 12a to the drug container.

The label 12a includes a first drug name section 20a in a first orientation, a second drug name section 22a in a second orientation, a third drug name section 24a in a third orientation, a drug concentration section 26a, a variable information section 28a, a graduation viewing section 30a and a trade dress section 32a. The first orientation, second orientation, and third orientation are different from each other to enable the information displayed to a user in such section (such as the name and the drug dose of the drug, etc.) to be upright, regardless of the position and orientation of the drug container as further discussed below.

The first drug name section 20a of the label 12a is substantially rectangular in shape and is positioned along a horizontal or substantially horizontal axis in the upper left-hand corner of the label 12a. When affixed to a syringe 40 as illustrated in FIGS. 4A and 4B, the first drug name section 20a is aligned with and oriented toward the port end 42 of the syringe 40. The first drug name section 20a includes a prominent display of the name of the drug. The color of the first drug name section corresponds to the color code established by the ASTM for that drug.

The second drug name section 22a includes the name of the drug repeated side-by-side along the section. The second drug name section 22a is positioned along the right side of the label 12a along a vertical or substantially vertical axis and extends transverse to or perpendicular to the orientation of the first drug name section 20a. As illustrated in FIGS. 4A, 4B, 4C, 4D and 5, when affixed to a syringe the second drug name section 22a is substantially aligned with and oriented along the flange 44 of the barrel of the syringe 40.

The third drug name section 24a includes the name of the drug. The drug name is repeated side-by-side along the section. The third drug name section 24a is positioned adjacent to and to the right of the second drug name section 22a along the right edge of the label and transverse or perpendicular to the orientation of the first drug name section 20a. The third drug name section 24a, however, is configured in an opposite or inverted orientation to the second drug name section 22a such that the drug name is the mirror image of the drug name in drug name section 22a in this embodiment. As illustrated in FIGS. 4A, 4B, 4C, 4D and 5, when affixed to a syringe, the third drug name section 24a is substantially aligned with and oriented toward the flange 44 of the barrel of the syringe 40.

Opposing orientations of the second drug name section 22a and the third drug name section 24a enables the name of the drug to be displayed in an upright position in two different orientations of the syringe (i.e., in each respective section, the letters of the drug or other information are positioned in an upright fashion with respect to that section) As illustrated in FIG. 4B, the name of the drug, "Midazolam," is oriented in an upright position in second drug name section 22a (relative to that section) when the needle port 42 of the syringe 40 is pointed in an upward direction. As illustrated in FIG. 4C, the name of the drug, "Midazolam," is oriented in an upright position in the third drug name section 24a (relative to that section) when the needle port of the syringe is pointed in a downward direction.

In the illustrated embodiment, the drug concentration section 26a includes the concentration or dosage strength of the drug, total amount of the drug in the device or container, the volume and type of the container, storage information, warning statements regarding the use of the contents and other information regarding the contents of the drug container.

In this illustrated embodiment, the variable information section 28a of the label is rectangular-shaped and is positioned immediately adjacent to and below the drug concentration section 26a of the label. The variable information section 28a is substantially white in color and (although not illustrated) includes information that varies among different drug administration safety devices for the same drug and concentration and volume of drug. Information displayed in this section 28a may, for example, include a bar code, lot number, expiration date of the drug, national drug code (NDC) number, size and type of the device or container, service code, the date the formulation was made, recipient information and any other suitable information. The variable information section 28a also includes information related to the manufacturer of the drug administration safety device, such as company name, company contact information, corporate dress and any other suitable information.

Figure 6:
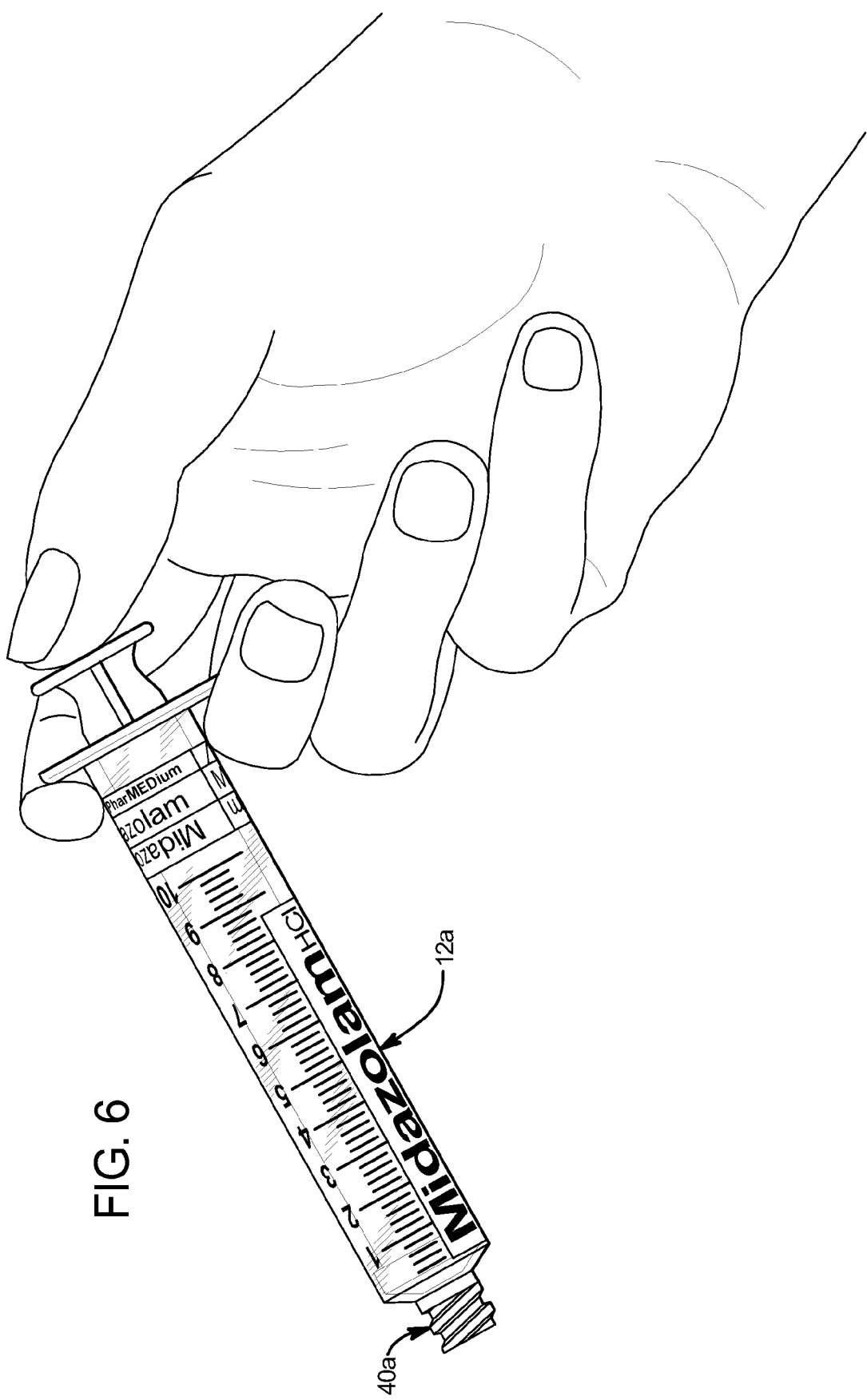
FIG. 6 is a perspective view of an embodiment of the label of the drug administration safety device affixed to a syringe in use by a user.

The graduation viewing section 30a is configured to reveal certain portions of the device or container that have information displayed on or affixed to the surface of the device or container itself. The graduation viewing section 30a is L-shaped forming the lower edge of the label 12a and dividing the first drug name section 20a, concentration section 26a and the variable information section 28a from the second drug name section 22a. As illustrated in FIGS. 4A and 6, when the label 12a is affixed to a syringe, the graduation viewing section 30a of the label 12a of the present disclosure reveals the graduation markings 46 on the syringe 40 as illustrated in FIG. 4A.

The trade name section 32a is positioned adjacent to and aligned with the third drug name section 24a and forms the right edge of the label 12a. When affixed to a syringe as illustrated in FIGS. 4A, 4B, 4C, 4D and 5, the trade name section 32a is substantially aligned along and oriented toward the flange 44 of the barrel of the syringe 40. The trade name section 32a includes the company name and trademark corporate dress.

It should be appreciated that each drug administration safety device of the present invention may be manufactured individually or in groups. More specifically, in one embodiment each label, adhesive and backing is made as an individual device. In another embodiment, a plurality of drug administration safety devices are made together in that they share the same backing. These can be made in a roll for ease of storage and use or application to drug containers.

The label may be made of any suitable material and weight or thickness. The label includes a material suitable for reproduction of graphics and lettering onto its surface through any suitable printing process including mechanical, electronic such as electrostatic, magnetographic, ion or electron deposition, ink-jet printing, or any other suitable type of printing process. At least a portion of the label 12a includes a material that is resistant to moisture. In one embodiment, the label is a plastic. At least a portion of the label 12a includes a synthetic plastic material such as a biaxially oriented polypropylene. The label 12a of the illustrated embodiment is substantially clear or transparent. It should be appreciated, however, that at least a portion of the label may be opaque and include any suitable color.

The material of the label may be made at any weight or thickness suitable for manipulating the label to be affixed in a suitable manner to the surface of the drug container and durable for use of the drug container. In an embodiment, the thickness of the substrate is at least about 0.2 to about 5 mil or about 1 to about 3 mil. The thickness of the substrate 12a of the drug administration safety device is about 2 mil.

It should be appreciated that the features described above are included in each of the embodiments of the drug administration safety device illustrated in FIGS. 2B, 2C, 2G, 2K, and 2M.

Referring to FIGS. 2D, 2E, 2F, 2H, 2I, 2J and 2L, in an embodiment, one or more different shapes, combination of shapes or positioning of shapes are associated with a specific drug concentration of the same drug. In addition to the features described above, the embodiments of the drug administration safety device illustrated in FIGS. 2D, 2E, 2F, 2H, 2I, 2J and 2L include one or more shapes displayed in their respective drug concentration sections 26d, 26e, 26f, 26h, 26i, 26j and 26l to differentiate different concentrations of the same drug.

Figure 1:
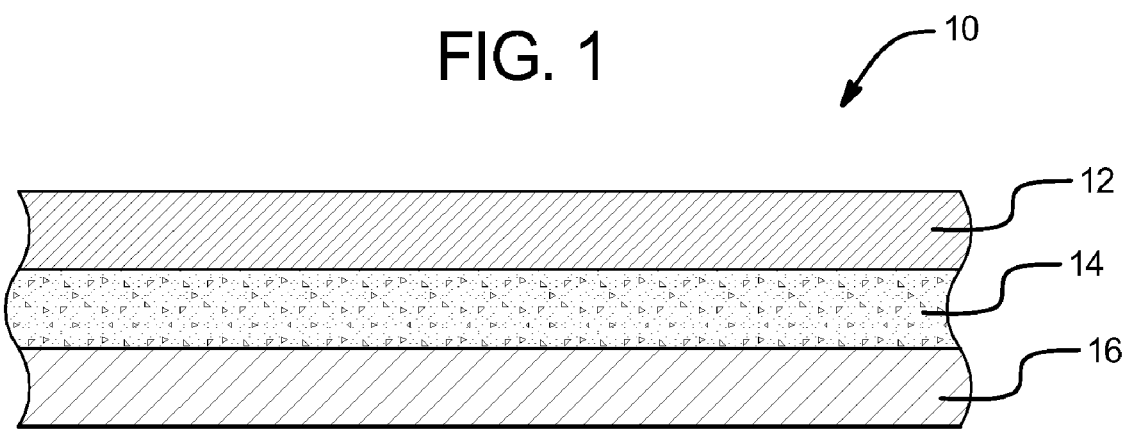
FIG. 1 is a cross-section of a drug administration safety device of an embodiment of the present disclosure.
Figure 2A:
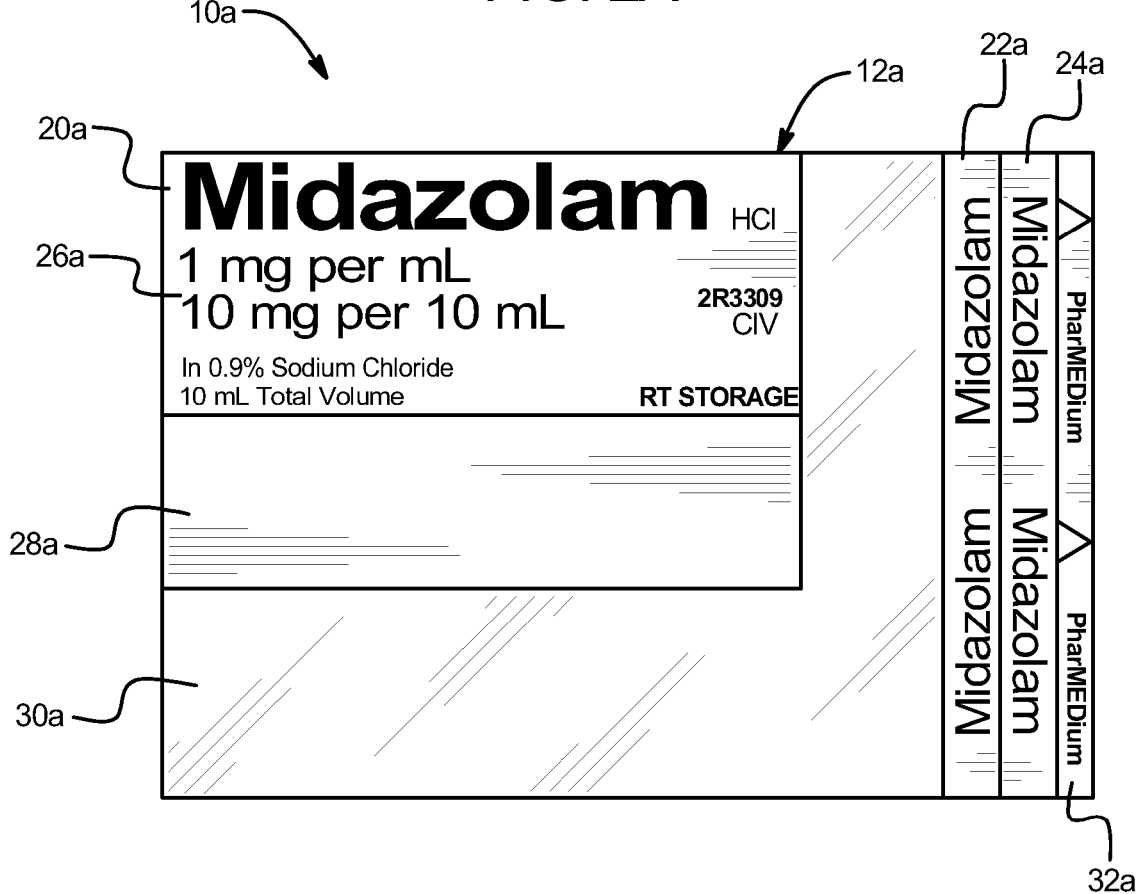
Figure 2B:
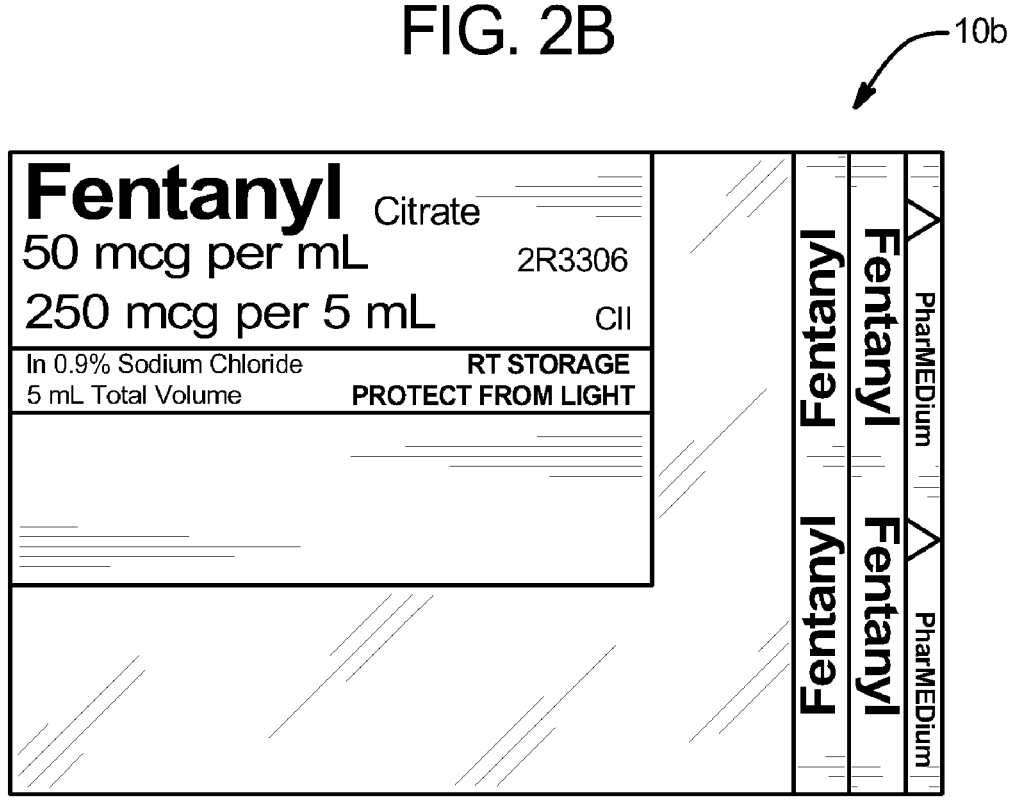
Figure 2C:
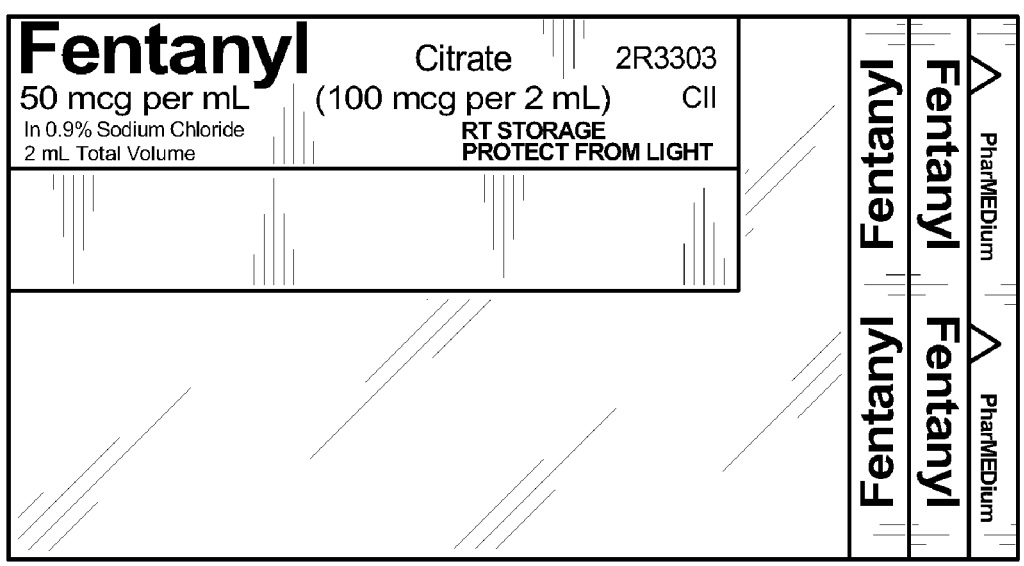
Figure 2G:
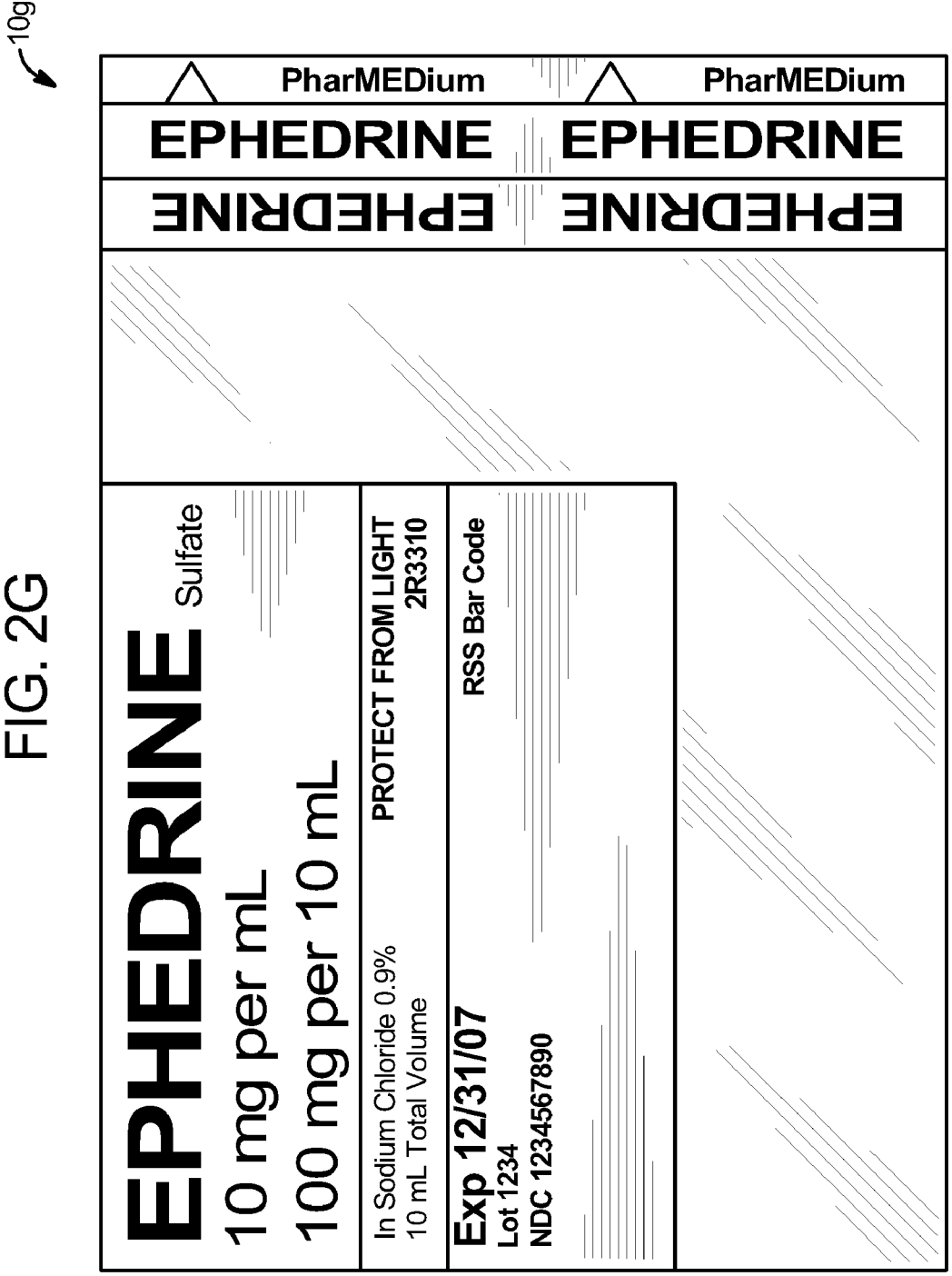
Figure 2H:
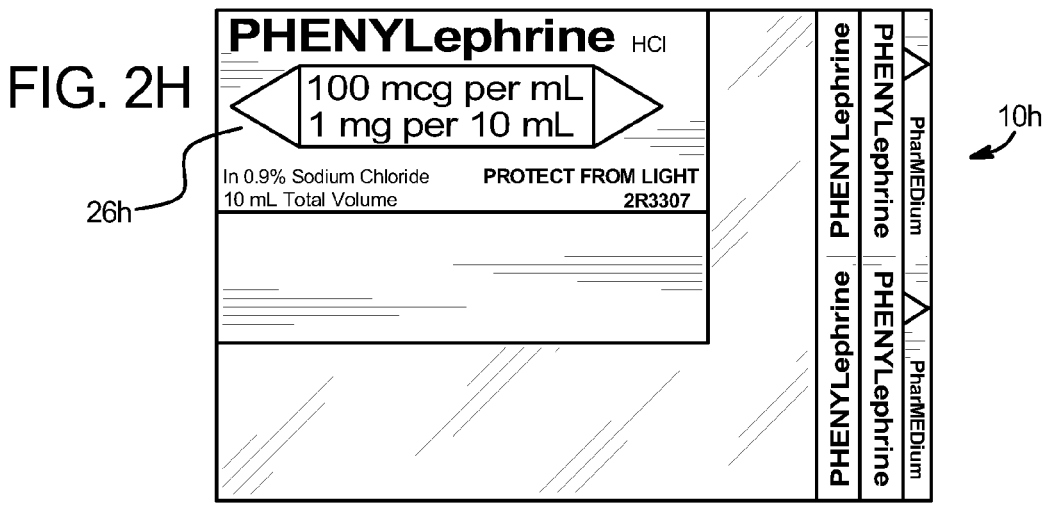
Figure 2I:
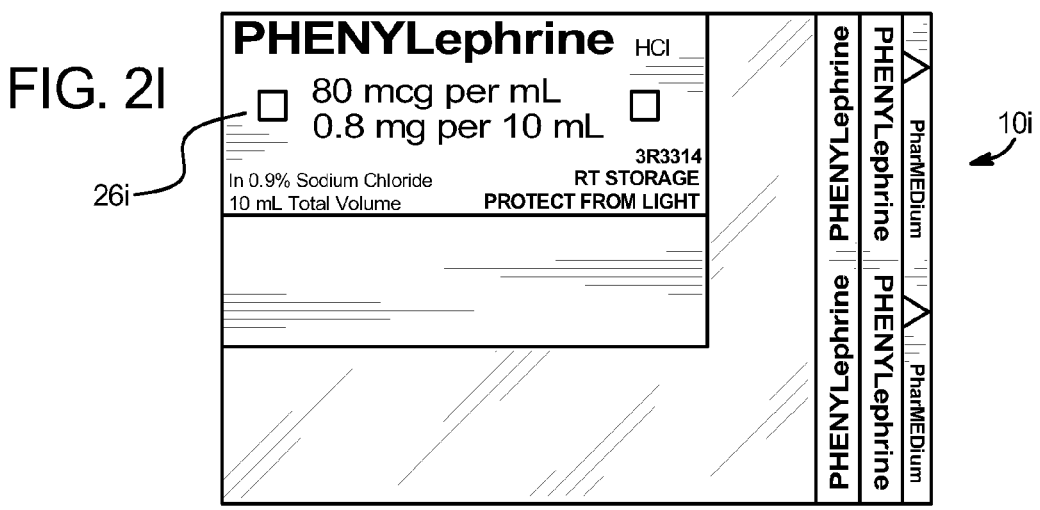
Figure 2J:
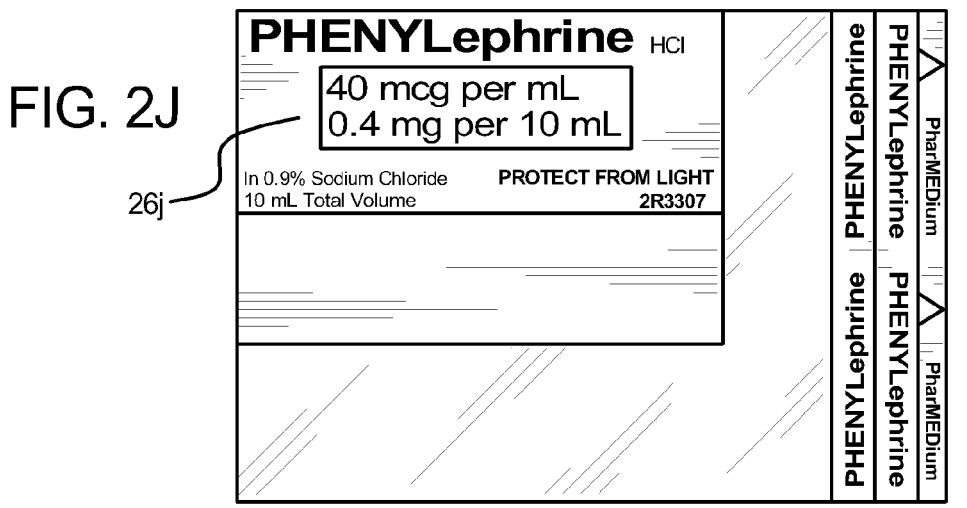
Figure 2K:
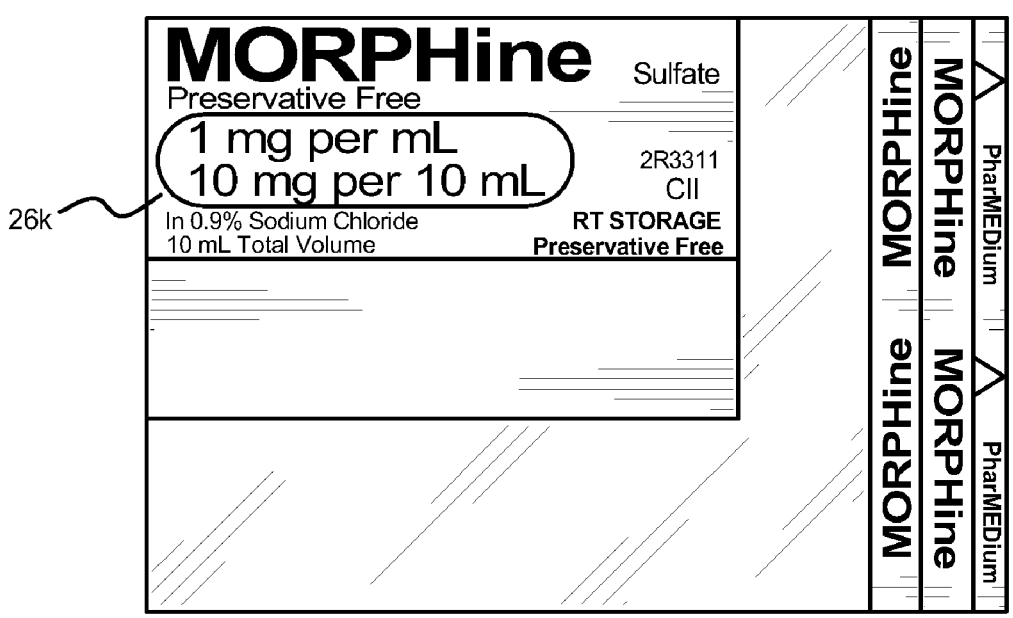
Figure 2L:
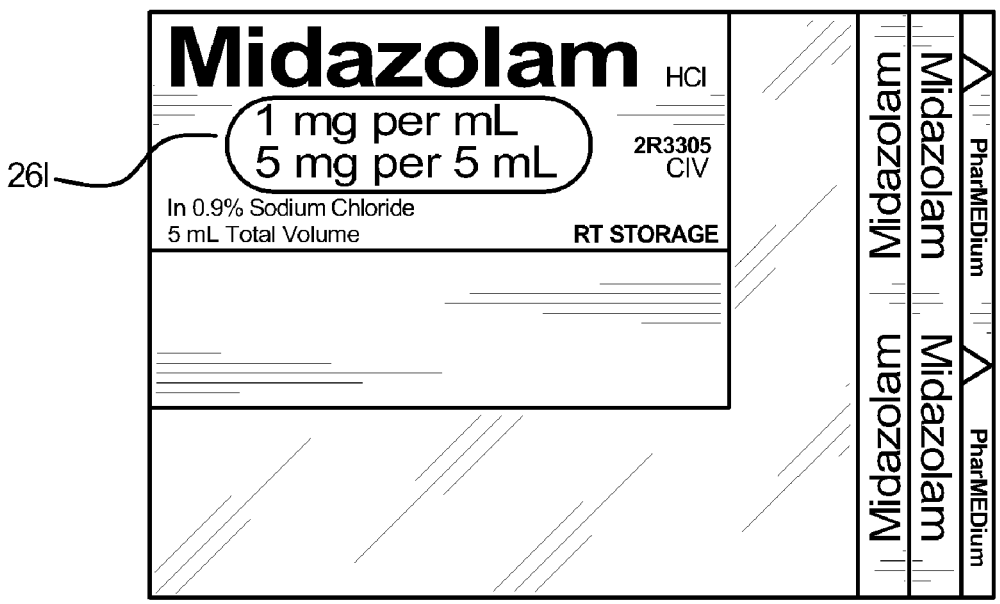
Figure 5:
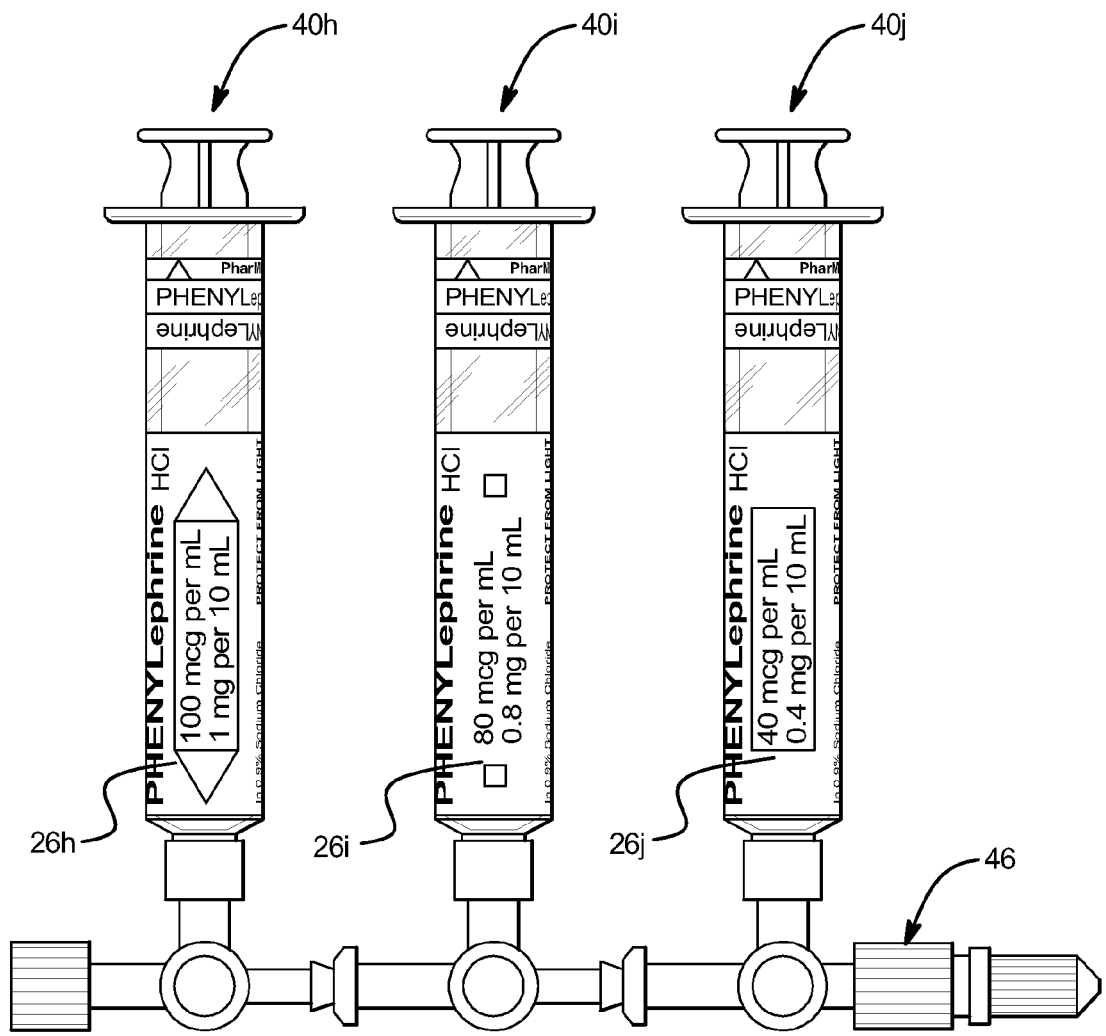
FIG. 5 is a perspective view of embodiments of the labels of the drug administration safety devices affixed to syringes in place on a three-port stopcock manifold.

For example, FIG. 5 illustrates three labels 12h, 12i and 12j, illustrated in FIGS. 2H, 2I and 2J, respectively, operatively affixed to three respective syringes 40h, 40i and 40j each secured to three-port stopcock manifold 46. Although the drug name of each label is the same, the concentration of the drug is different for each syringe. In particular, the label 12*h* on syringe 40*h* includes a concentration of "100 mcg per mL," the label 12*i* on syringe 40*i* includes a concentration of "80 mcg per mL" and the label 12*j* on syringe 40*j* includes a concentration of "40 mcg per mL," respectively. In the illustrated embodiment, the different concentrations of Phenylephrine are distinguished from one another by one or more shapes or pattern of shapes associated with the concentration information of the label. Label 12*h* includes a combination of triangles and a rectangle to differentiate the concentration of syringe 40*h* from the concentrations of the other syringes 40*i* and 40*j*. Label 12*i* includes a combination of two squares on either side of the concentration of syringe 40*i* to distinguish the concentration from the concentrations of syringes 40*h* and 40*j*. Label 12*j* includes a rectangle outlining the concentration of syringe 40*j* to distinguish the concentration from the concentrations of syringes 40*h* and 40*i*. It should be appreciated that the absence or presence of one or more different shapes, combination of shapes or positioning of shapes associated with a specific drug concentration of the same drug enables a user of the drug container to distinguish between different concentrations of the same drug within similar containers.

Figure 3A:
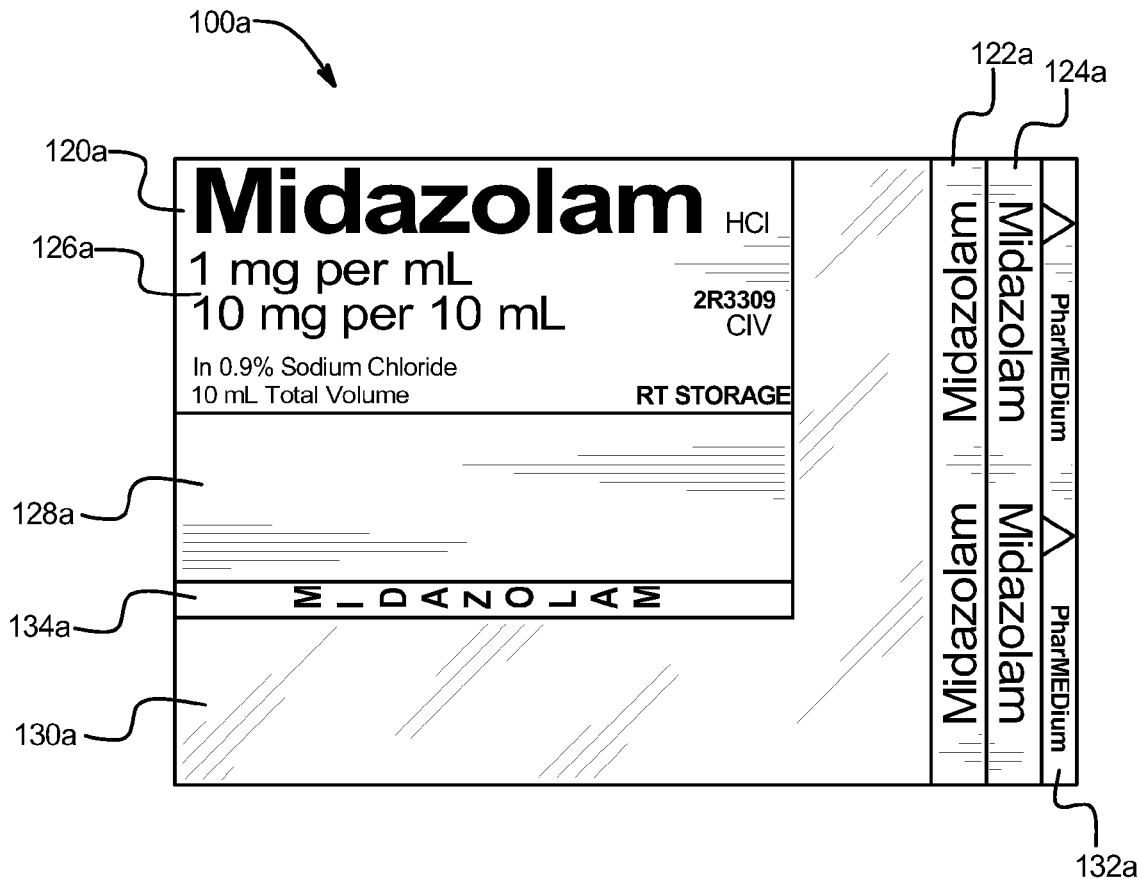
Figure 3B:
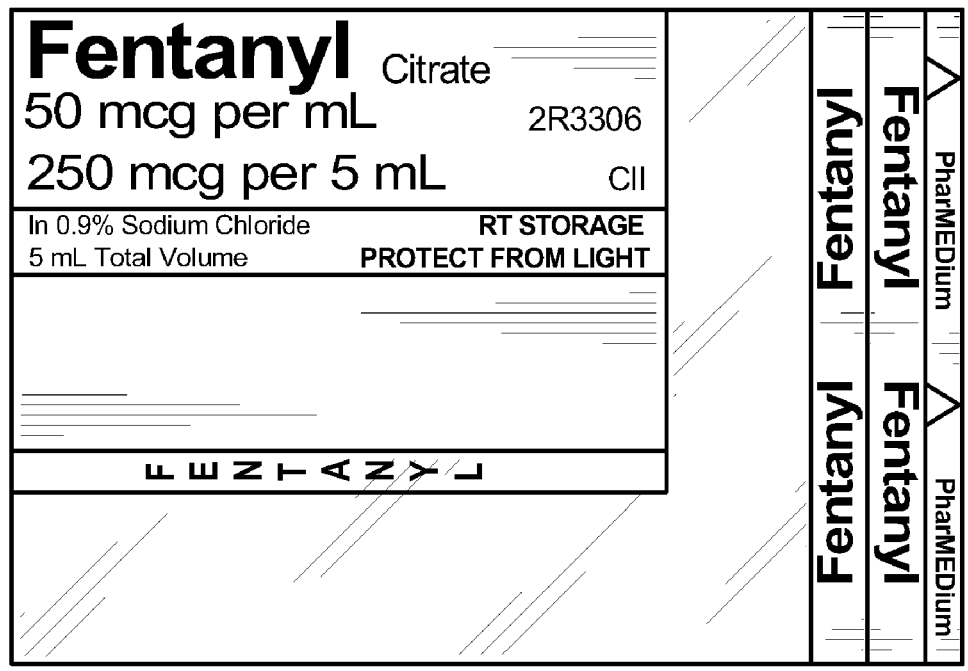
Figure 3C:
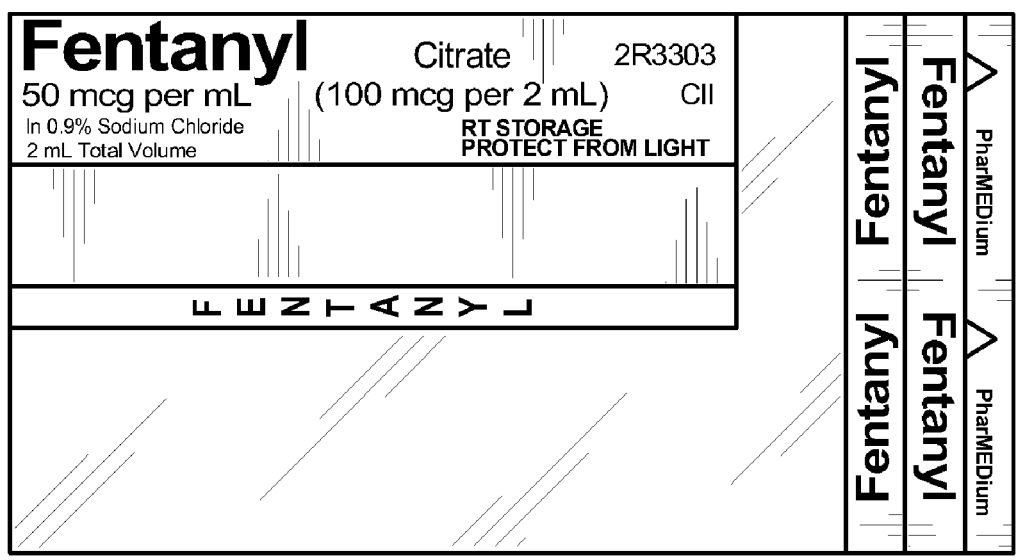
Figure 3G:
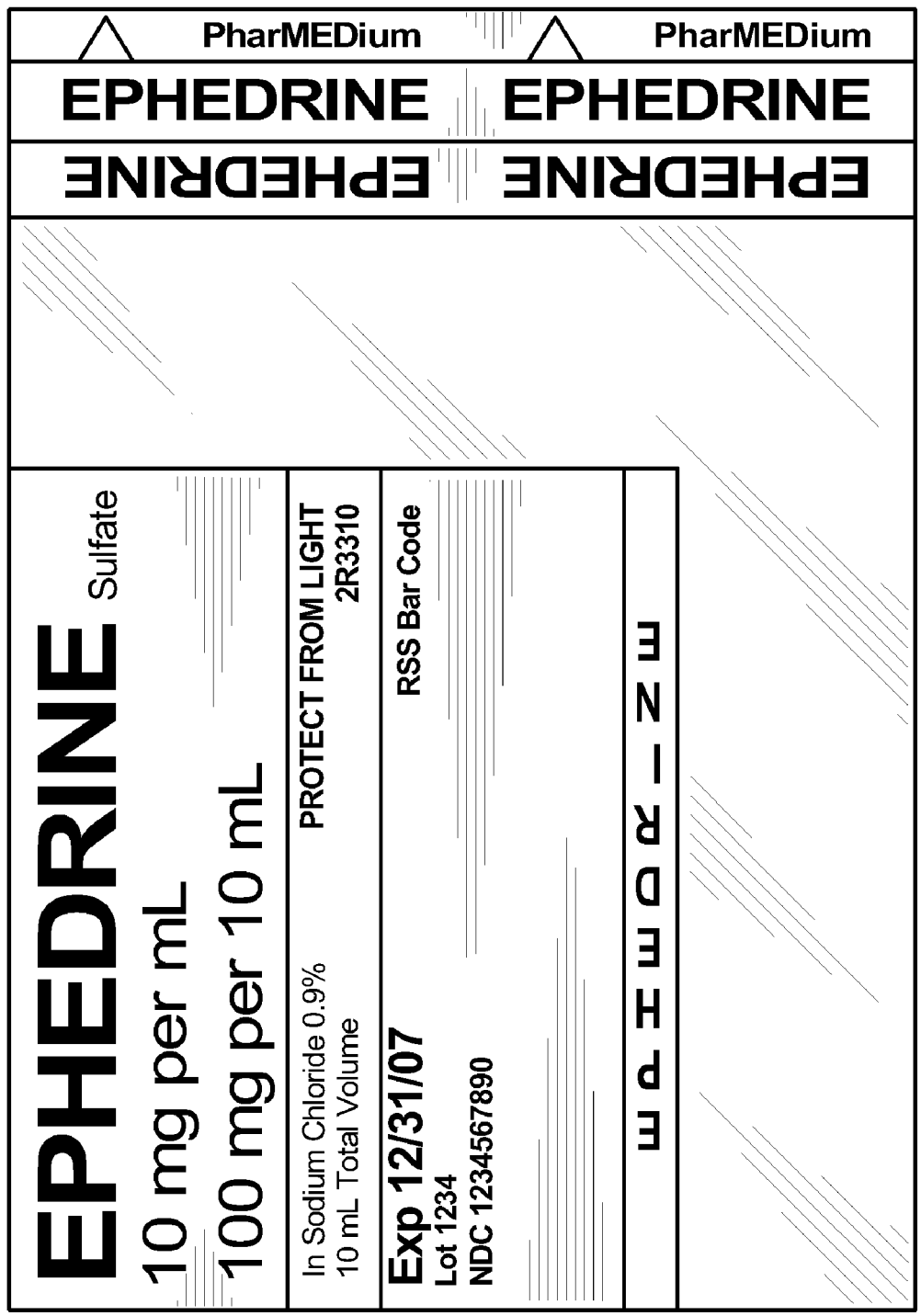
Figure 3H:
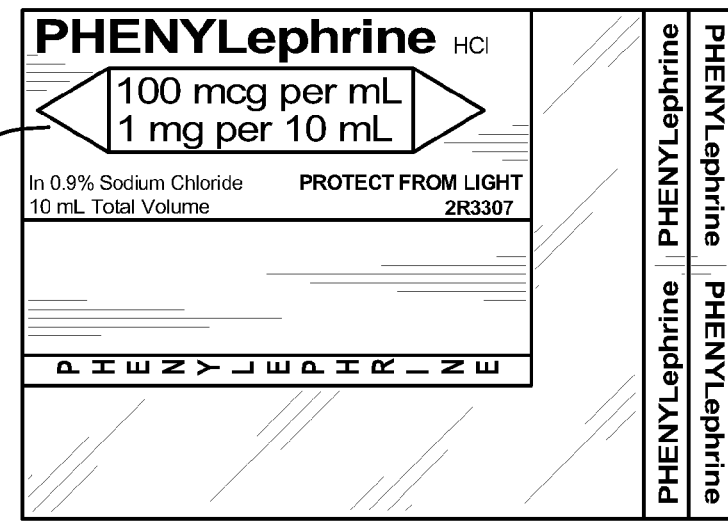
Figure 3I:
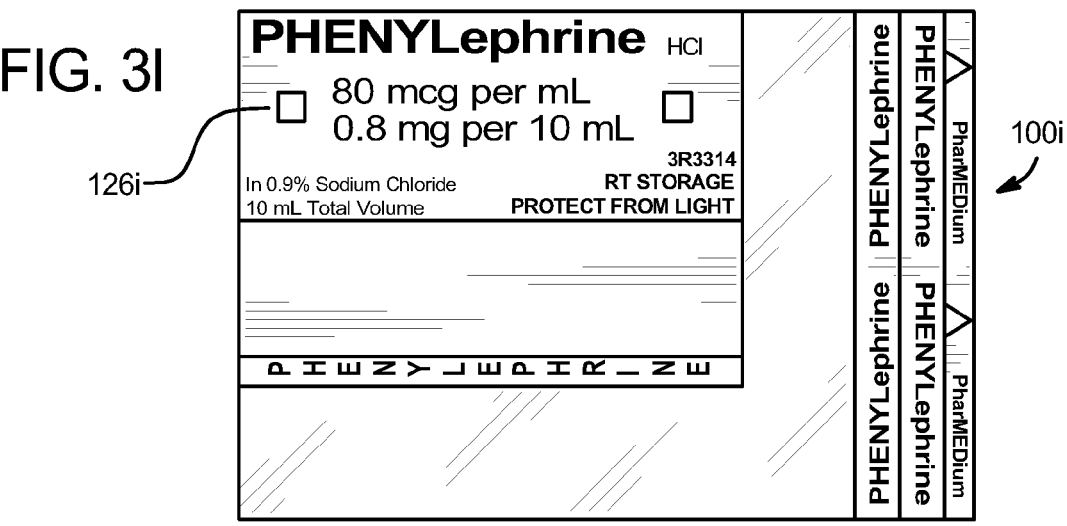
Figure 3J:
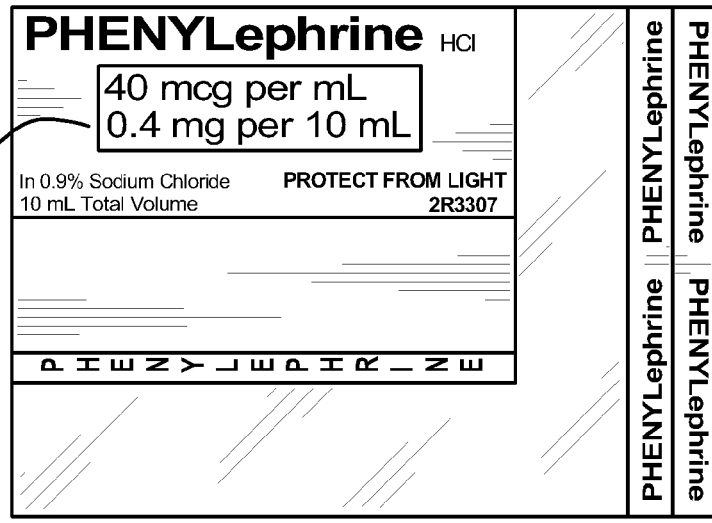
Figure 3K:
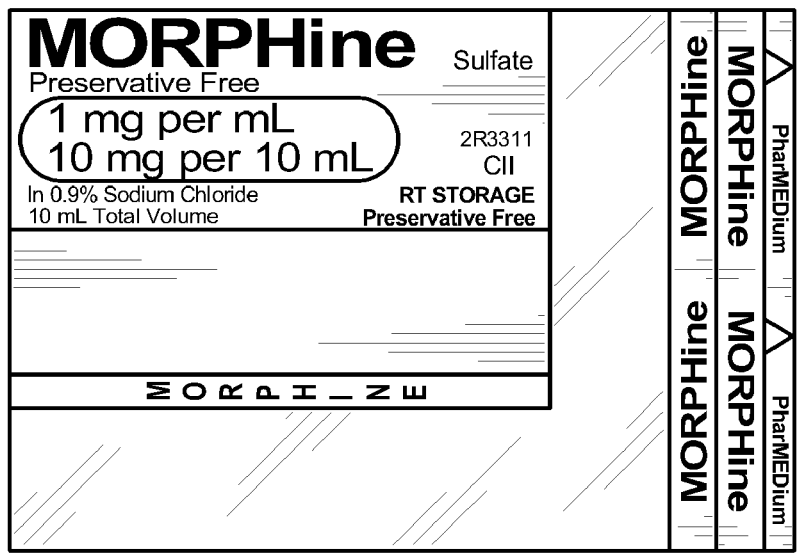
Figure 3L:
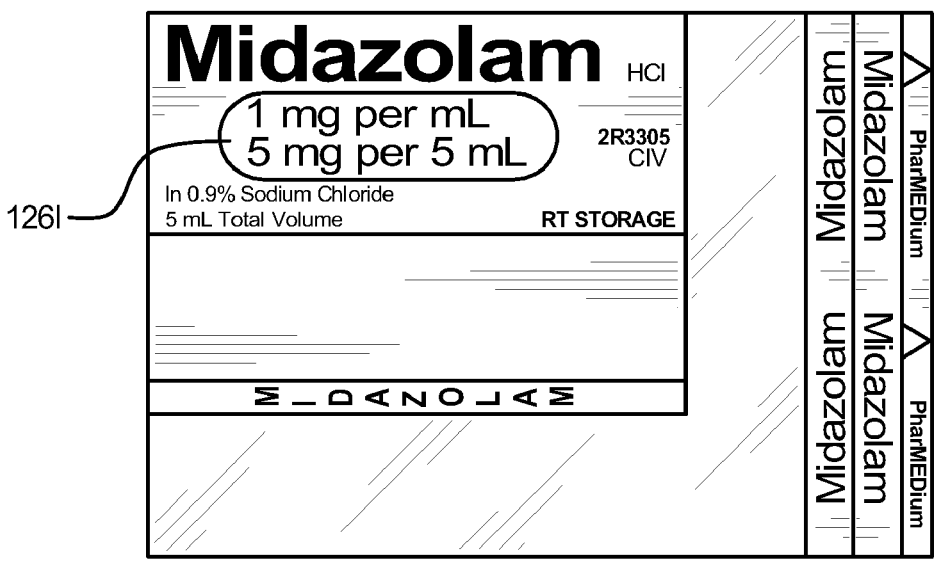
Figure 4D:
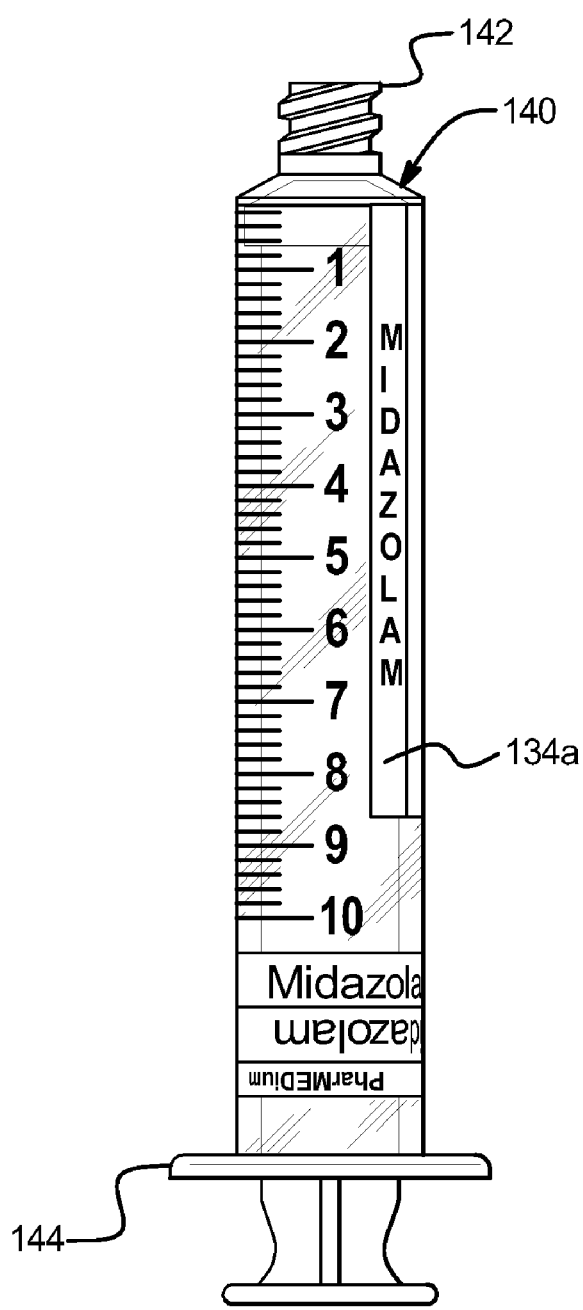
FIG. 4D is a perspective view of an alternative embodiment of the label of the drug administration safety device affixed to a syringe.

Referring now to FIGS. 3A and 4D, in a further embodiment of the drug administration safety device of the present disclosure, generally indicated by numeral 100*a*, in addition to a first drug name section 120*a*, a second drug name section 122*a* and a third drug name section 124*a* as described above, the label 112*a* includes a fourth drug name section 134*a*. The fourth orientation of the fourth drug name section 134*a* is different from the first orientation of the first drug name section 120*a*, a second orientation of the second drug name section 122*a* and a third orientation of the third drug name section 124*a*. Each of the letters in the name of the drug displayed in the fourth drug name section 134*a* of the label are positioned one on top of the other and aligned along the graduation viewing section 134*a*. When the label 112*a* is removed from its backing 16 and placed on a drug container such as a syringe 140, the user is able to view both the graduation markings and the drug name when operating the syringe. This embodiment also includes a drug concentration section 126*a* and a variable information section 128*a* and a trade name section 132*a*.

It should be appreciated that the features described above are included in each of the embodiments of the drug administration safety device illustrated in FIGS. 3B, 3C, 3G, 3K, and 3L except that no shape is used in the respective drug concentration sections. It should be further appreciated that the features described above are included in each of the embodiments of the drug administration safety device illustrated in FIGS. 3D, 3E, 3F, 3H, 3I, 3J and 3M except that different shapes are used in their respective drug concentration sections 126*d*, 126*e*, 126*f*, 126*h*, 126*i*, 126*j* and 126*m* to differentiate different concentrations of the same drug.

FIG. 6 illustrates an example of one of the disclosed embodiments attached to a syringe in use by a user. As illustrated in FIGS. 4A, 4B, 4C, 4D and 6, the features of the disclosed embodiments combine to enable the user to view the name of the drug in virtually any orientation of the syringe while maintaining the view of markings on the syringe and not interfering with the function of the syringe.

It should be appreciated that the label of the drug administration safety device may be other suitable sizes and shapes. It should also be appreciated that the sections may be dimensioned and oriented in other suitable manners in relation to one another and in relation to the device or container. Although the sections including the drug name are positioned on the label in different orientations, it should be appreciated that other information may be displayed in different orientations. In addition, in an alternative embodiment, one or more of the sections of the label of the drug administration safety device may be affixed to the device or container as separate sections that are positioned on the same device or container as described herein.

It should also be appreciated that information displayed in the sections of the label may include identification information, information describing the contents of the device or any other suitable information informing a user how to use the contents of the device or container. The information may be presented on the label in any suitable form of lettering, numbering, symbols, graphics and combinations thereof in any suitable color or shade or any other suitable form of conveying information to the user. In various embodiments, "tall-man" lettering is employed to emphasize certain distinguishing portions of the drug name. For example, in FIGS. 2H, 2I and 2J, the first six letters of the drug name morphine ("PHENYL") are displayed in all caps to distinguish the drug name from other drugs ending in "-ephrine" such as "Epinephrine."

In an alternative embodiment, the drug administration safety device includes a label configured to be placed on an IV bag or container. The label of the drug administration safety device of one such embodiment may be a paper face stock which may be coated for thermal resin acceptance. It should be appreciated that the drug administration safety device may include any suitable mechanism of affixing the drug administration safety device to a drug delivery device or container.

Figure 7:
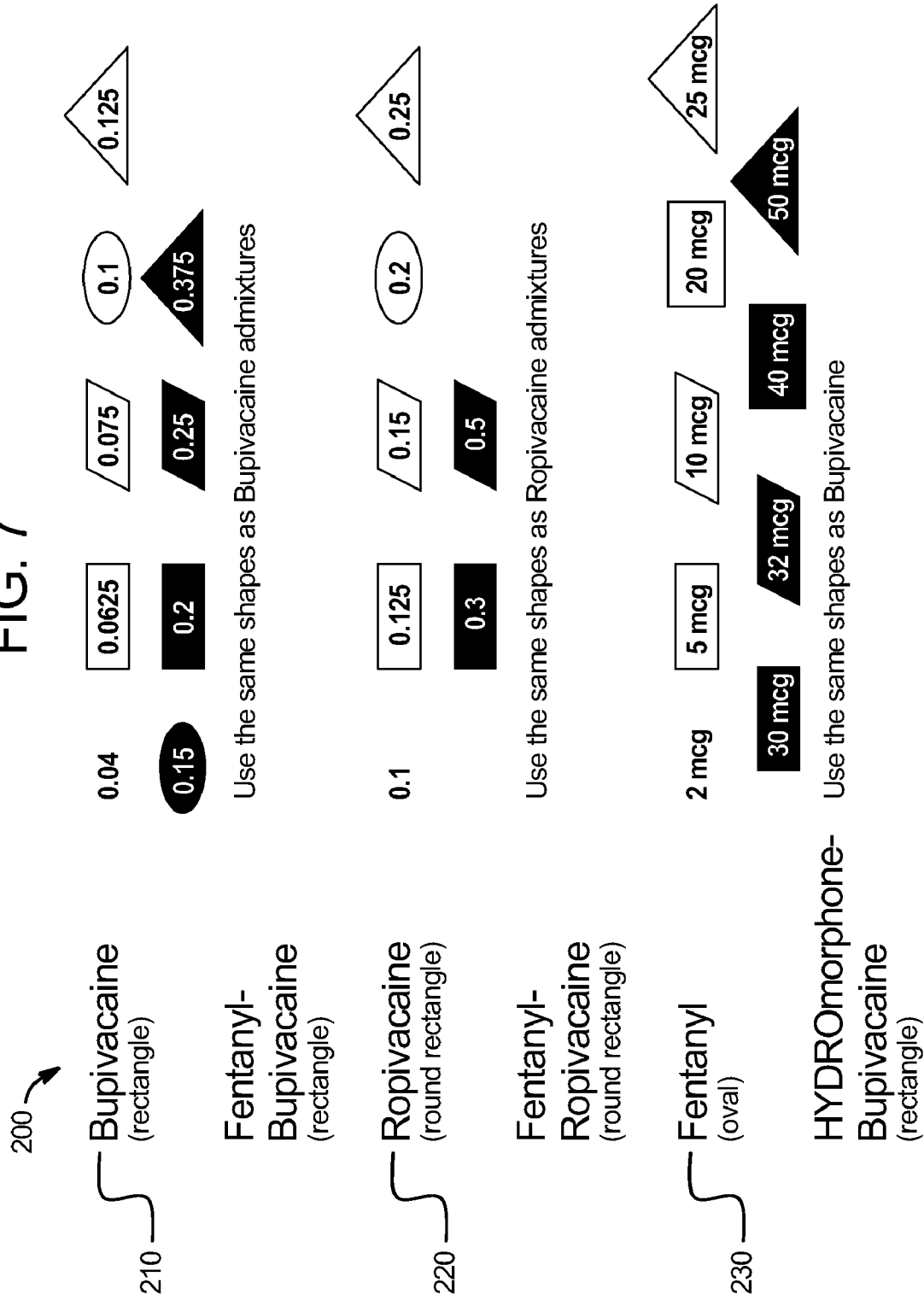
FIG. 7 is a plan view of a scheme for differentiating information on drug administration safety devices.

Referring now to FIG. 7, the present disclosure provides systems and methods of differentiating information on drug administration safety devices having similar information. In an embodiment, a scheme of shapes, colors and shades of shapes is developed for different concentrations of the same drug contained in a plurality of devices or containers. Each dose of the same drug is associated with a different shape or reverse printing within the shape. For example, the shape may include a color that contrasts with the color of the information associated with the shape such as white lettering in a black shape. The shape corresponding to the dose of the drug is displayed in the drug concentration section of the label for that drug.

FIG. 7 illustrates a labeling scheme for distinguishing between different doses for each of the drugs, Bupivacaine, Ropivacaine and Fentanyl. As illustrated in FIG. 7, a series of shapes and shapes with reverse printing is used to distinguish different concentrations of the same drug. It should be appreciated that one dose may distinguished from the other doses by not having any shape associated with the dose.

The labeling scheme 210 for the drug Bupivacaine for example includes a different shape or shape with reverse printing for each of nine different doses from "0.04," to "0.375". For each dose either no shape or a different shape or reverse printing within the shape is used to distinguish each different concentration. According to the scheme illustrated in FIG. 6 a dose of "0.04" does not appear within a shape; a dose of "0.0625" appears within a rectangle, a dose of "0.075" appears within a parallelogram; a dose of "0.1" appears within an ellipse; a dose of "0.125" appears within a triangle; a dose of "0.15" appears within an oval in reverse printing, a dose of "0.2" appears within a rectangle in reverse printing, a dose of "0.25" appears within a parallelogram in reverse printing and a dose of "0.375" appears within a triangle in reverse printing.

The scheme illustrated in FIG. 7 also includes the same scheme or sequence of shapes for increasing concentrations or doses of other drugs. In other words, the sequence of no shape, rectangle, parallelogram, ellipse, triangle, ellipse of reverse printing, rectangle with reverse printing, parallelogram with reverse printing and triangle with reverse printing for increasing doses of Bupivacaine may be the same sequence for increasing doses of other drugs. As illustrated in FIG. 7, the labeling scheme for Bupivacaine 210 is also used for different doses of Fentanyl-Bupivacaine. Alternatively, the sequence of shapes may be different for increasing doses of each drug such as for the Ropivacaine scheme 220 and Fentanyl scheme 230 illustrated in FIG. 7.

It should be appreciated that any suitable shapes, shading within the shapes, patterns of shapes, positions of the shapes in relation to information and or combinations thereof may be included in a labeling scheme for a particular drug to distinguish different doses of that drug.

Figure 8:
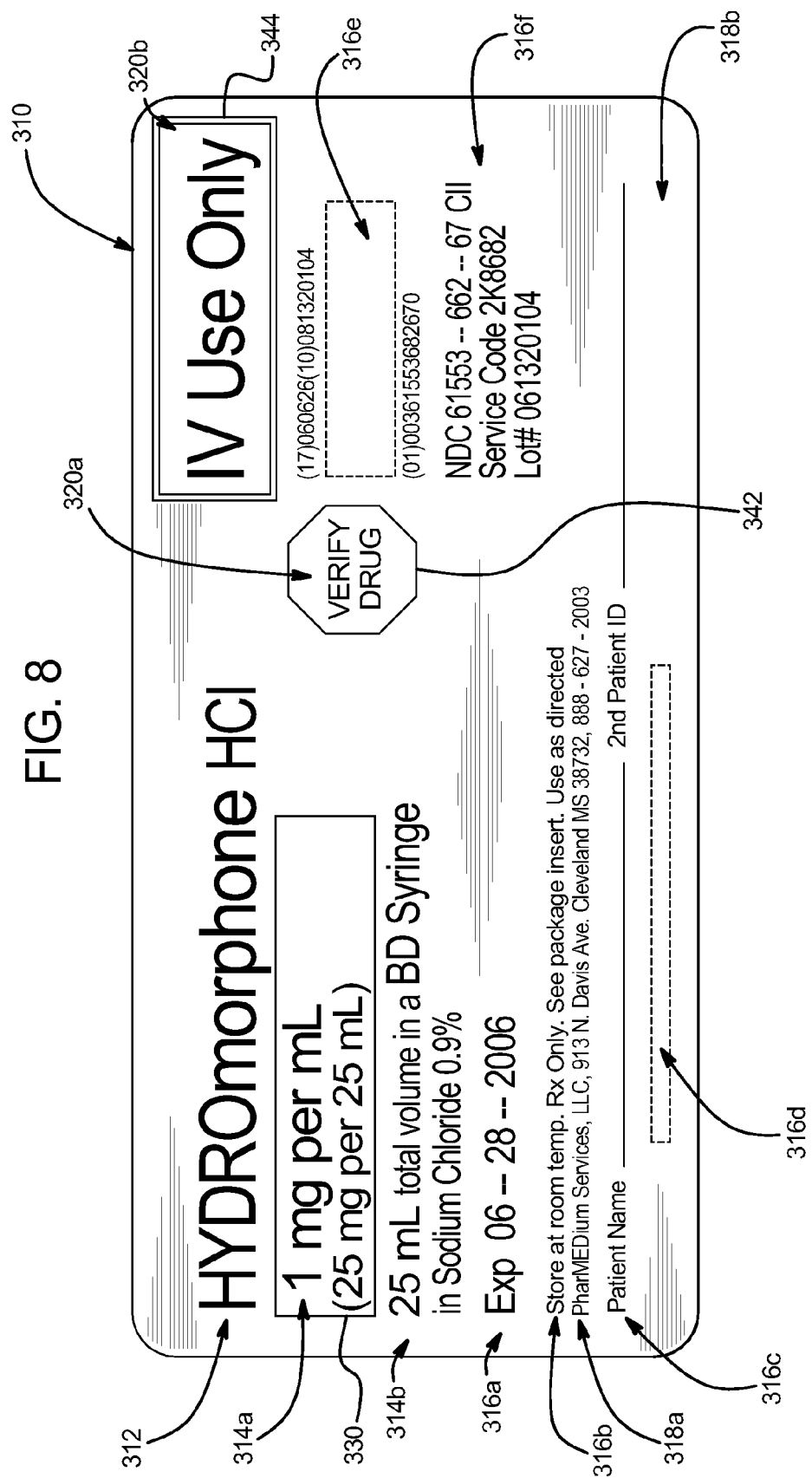
FIG. 8 is a plan view of a drug administration safety device of an embodiment of the present disclosure.

Referring now to FIGS. 8 through 42, in other embodiments, the drug administration safety device includes a label configured to be placed on any suitable surface of a drug storage or delivery device or container such as an IV bag, a cassette, a drug vial, syringe, or any other device or container containing an agent or drug. In an embodiment, the label includes any feature or combination of features disclosed herein. For example, as illustrated in FIG. 8, the label information on label 310 may include one or more drug name sections 312, drug concentration sections 314 and 314b, variable information sections 316a, 316, b, 316c, 316d, 316e and 316f, manufacturer, trademark and branding sections 318a and 318b and warning statement sections 320a and 320b in one or more orientations.

Figure 11:
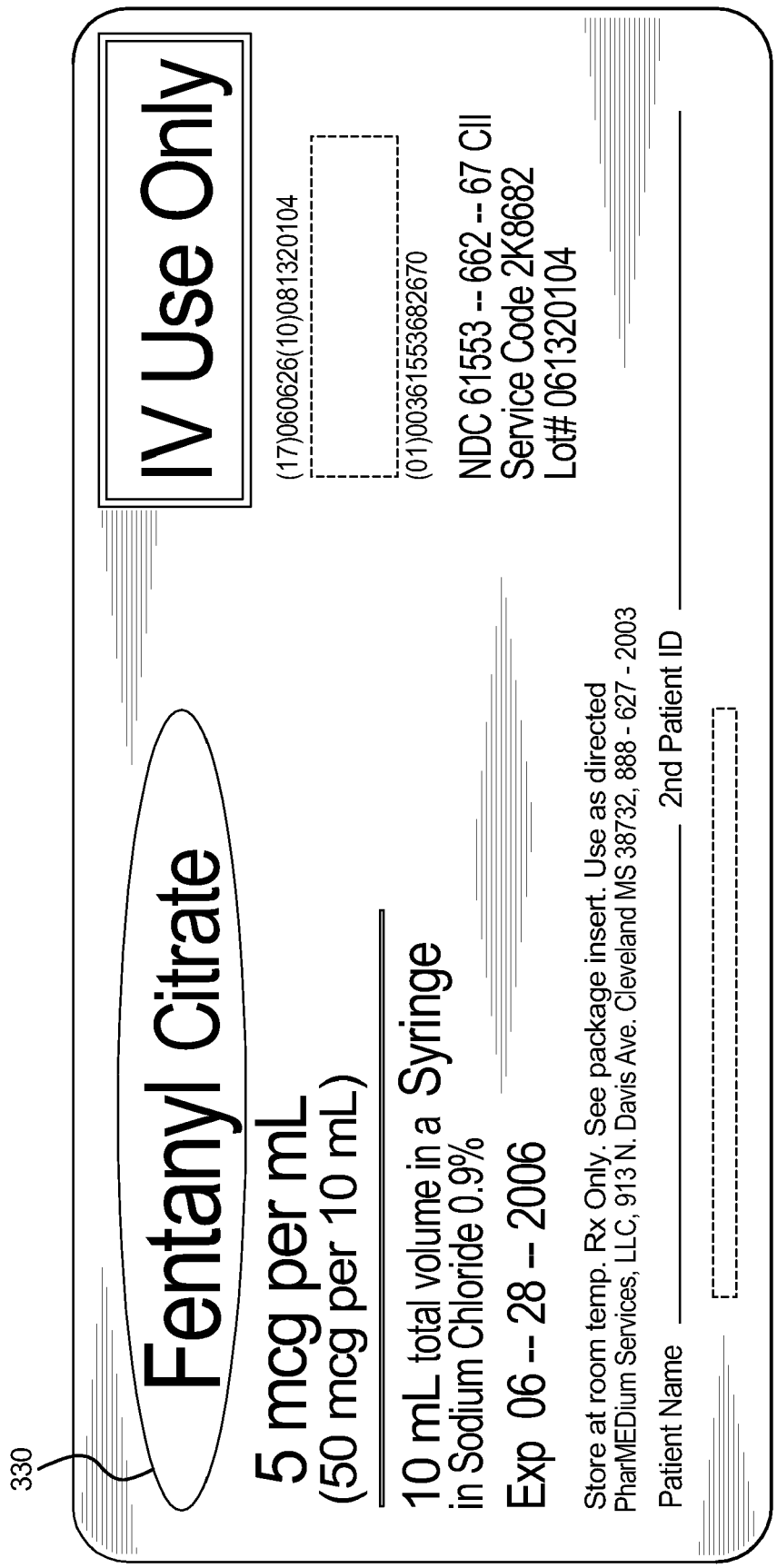
FIG. 11 is a plan view of a drug administration safety device of an embodiment of the present disclosure.
Figure 12:
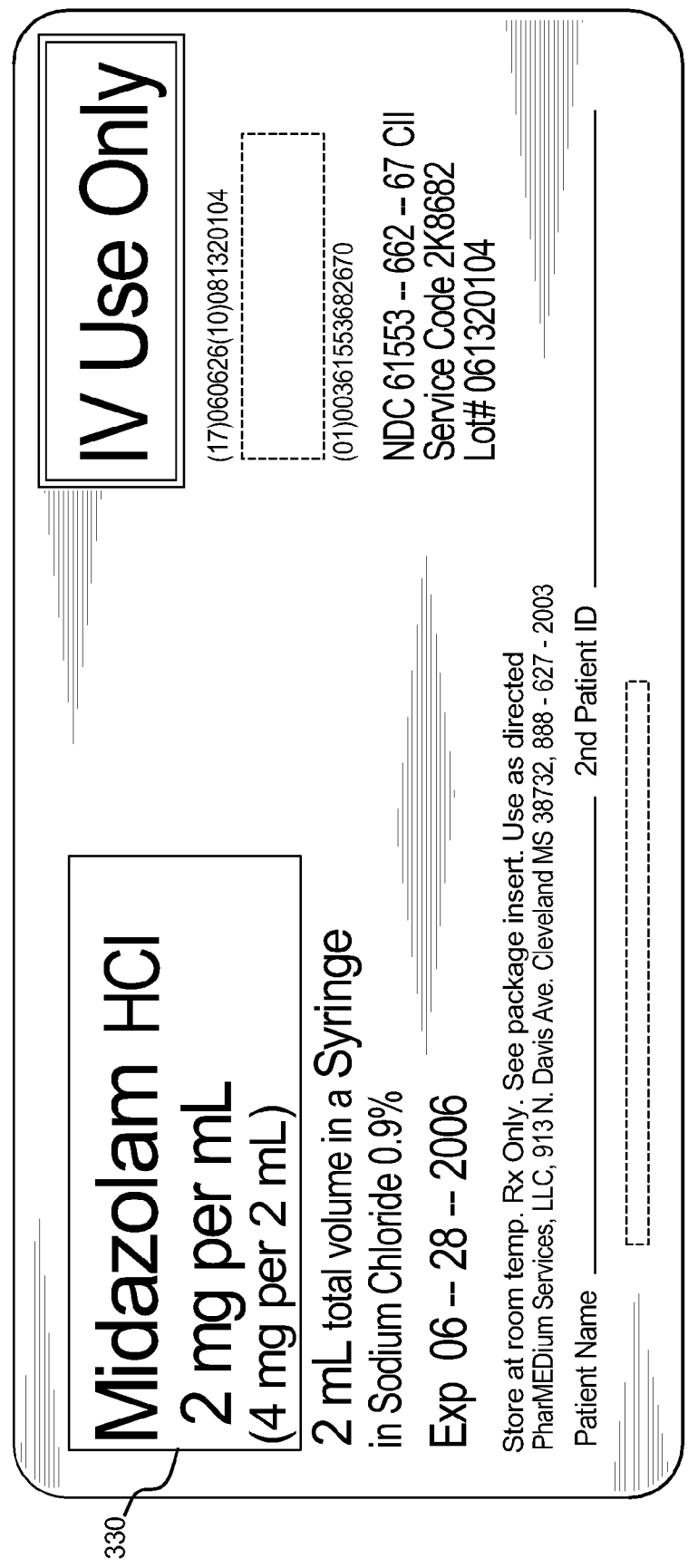
FIG. 12 is a plan view of a drug administration safety device of an embodiment of the present disclosure.

As illustrated, shapes are used to distinguish between different information presented on the label, such as names of drugs and doses of drugs. As illustrated in FIG. 8, for example, in an embodiment, the label information is situated within a shape. It should be appreciated that in one embodiment the label information within the shape is in reverse printing. The drug information situated in shape 330 may be the drug concentration as illustrated in the embodiment of FIG. 8, the drug name, as illustrated in the embodiment of FIG. 11 or both as illustrated in FIG. 12.

Figure 10:
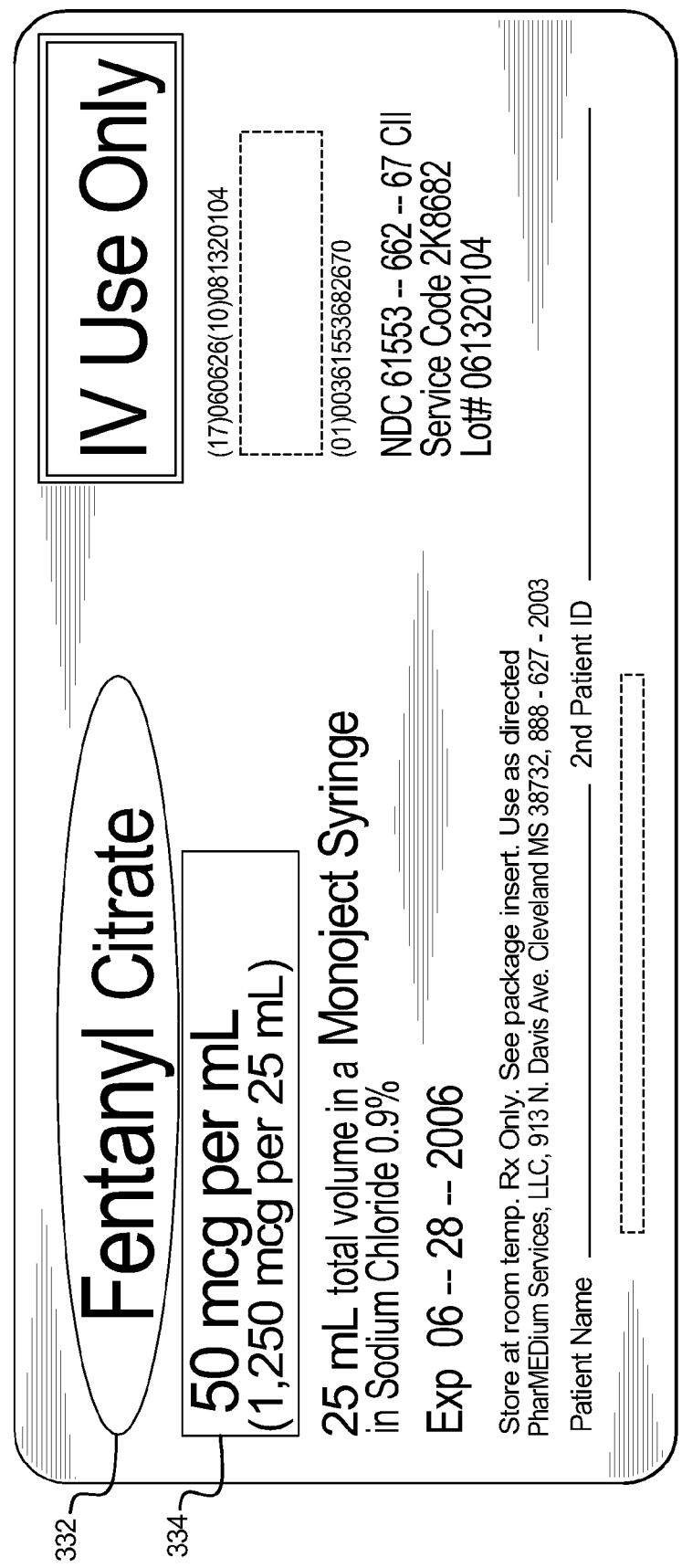
FIG. 10 is a plan view of a drug administration safety device of an embodiment of the present disclosure.
Figure 13:
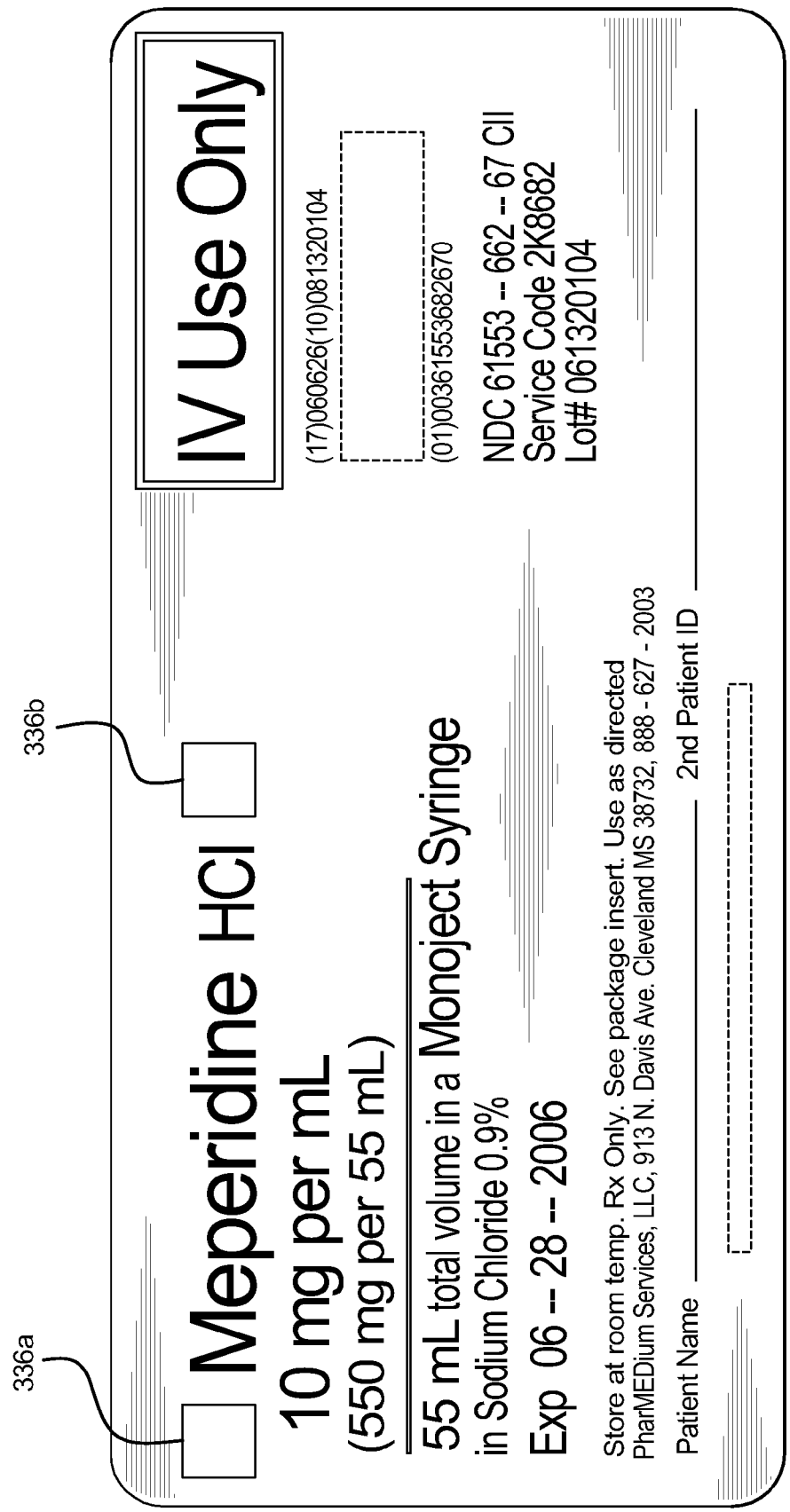
FIG. 13 is a plan view of a drug administration safety device of an embodiment of the present disclosure.
Figure 14:
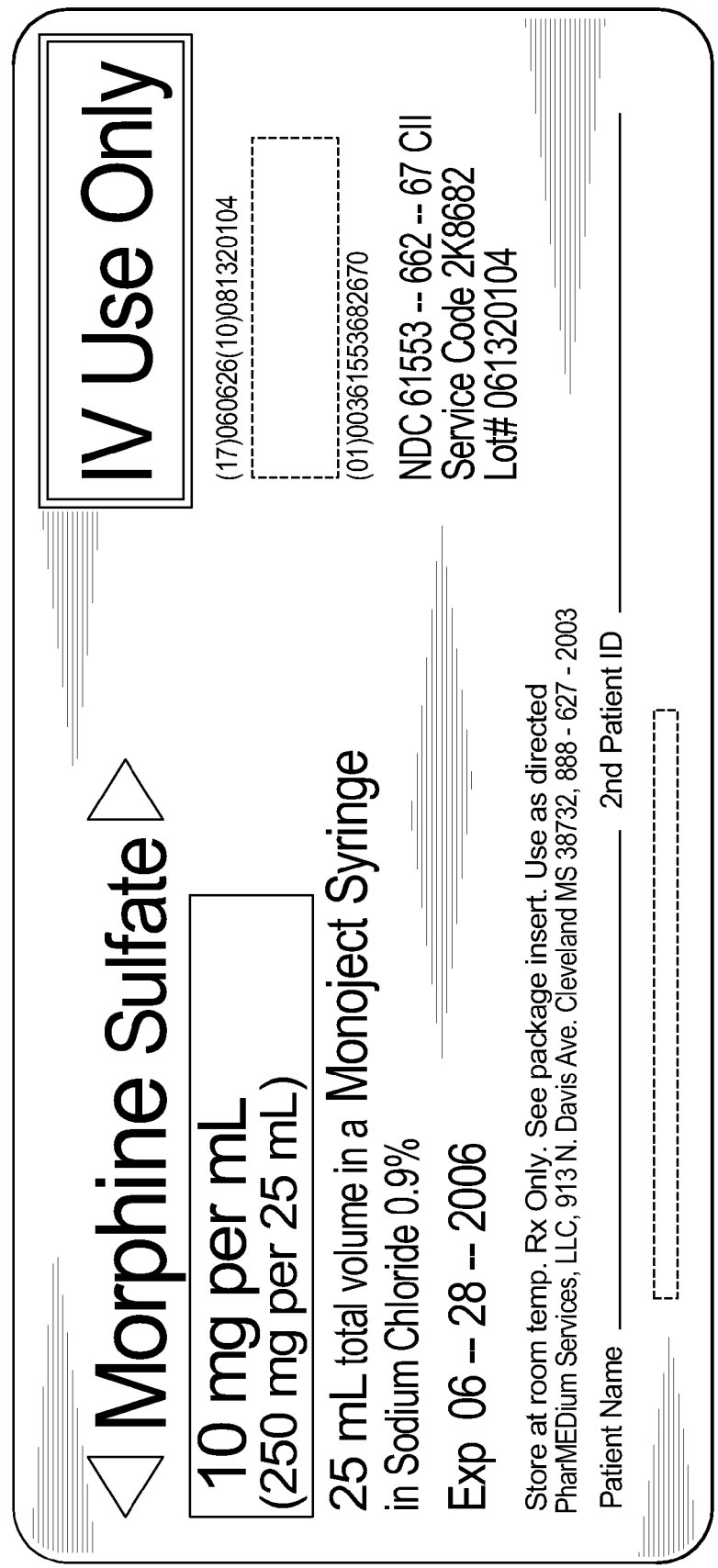
FIG. 14 is a plan view of a drug administration safety device of an embodiment of the present disclosure.
Figure 15:
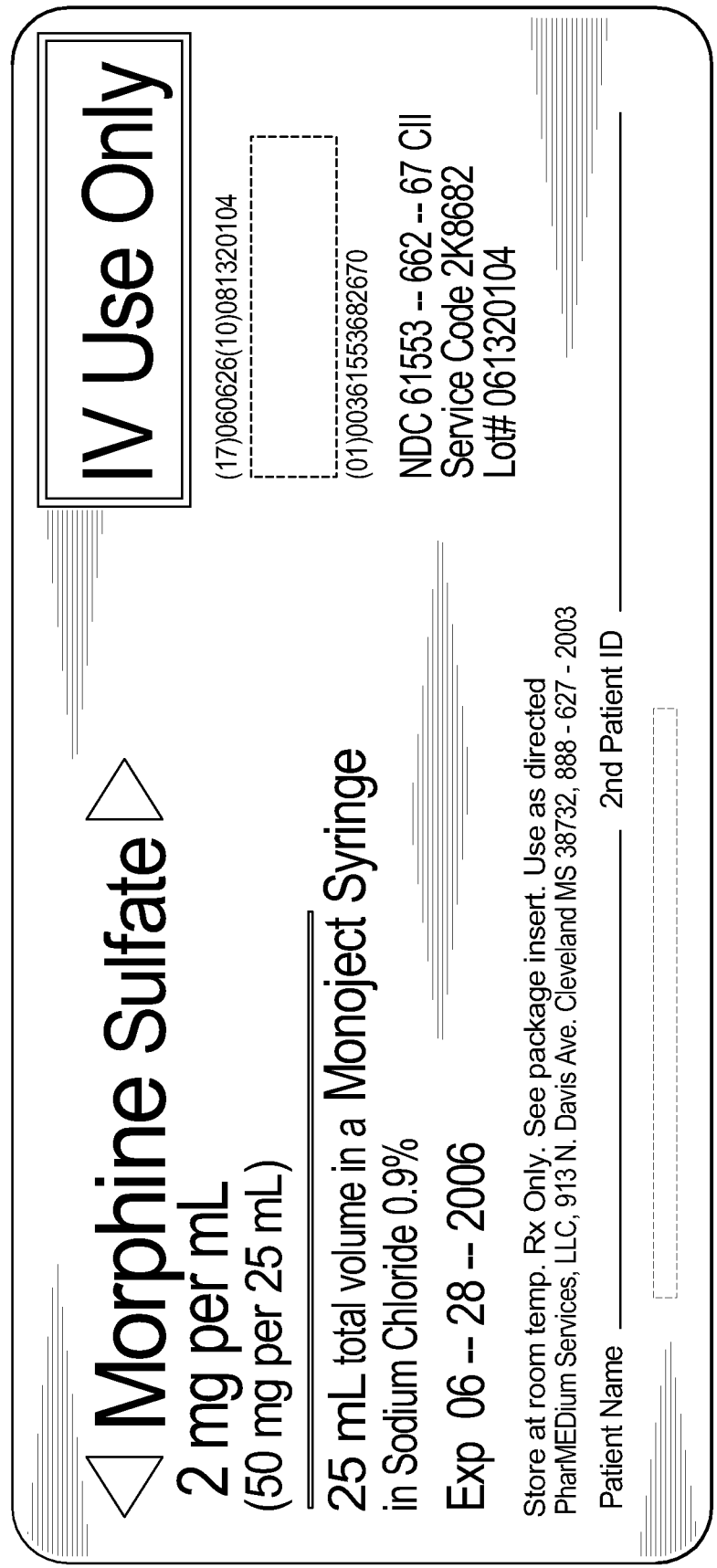
FIG. 15 is a plan view of a drug administration safety device of an embodiment of the present disclosure.
Figure 16:
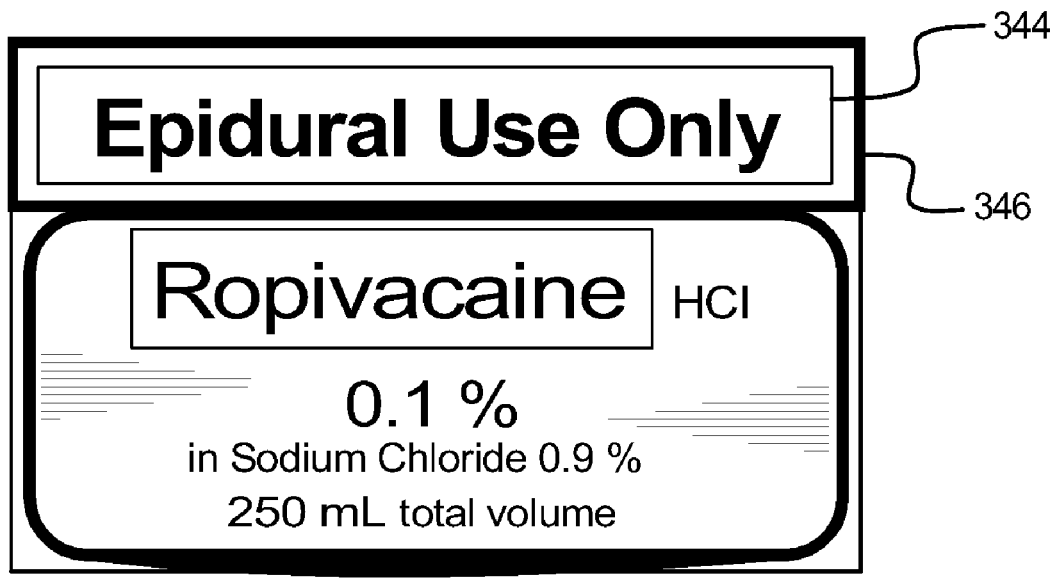
FIG. 16 is a plan view of a drug administration safety device of an embodiment of the present disclosure.
Figure 17:
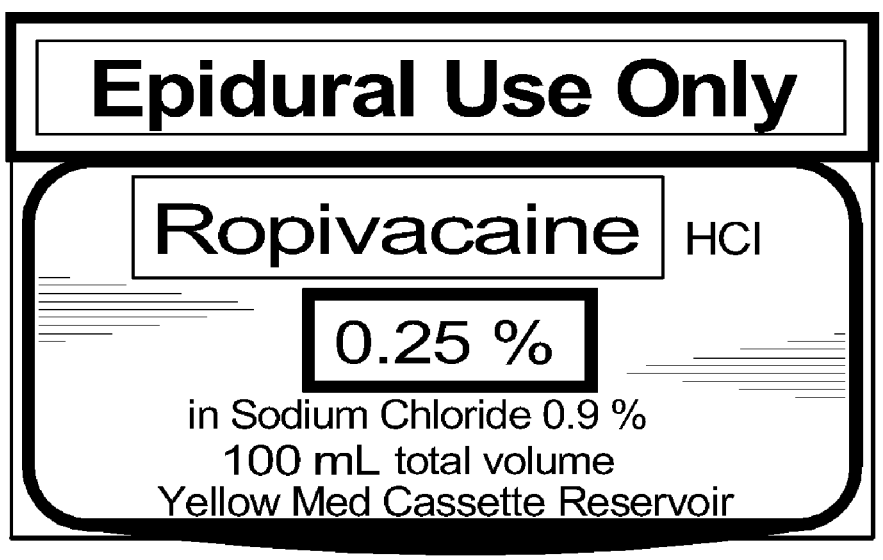
FIG. 17 is a plan view of a drug administration safety device of an embodiment of the present disclosure.
Figure 18:
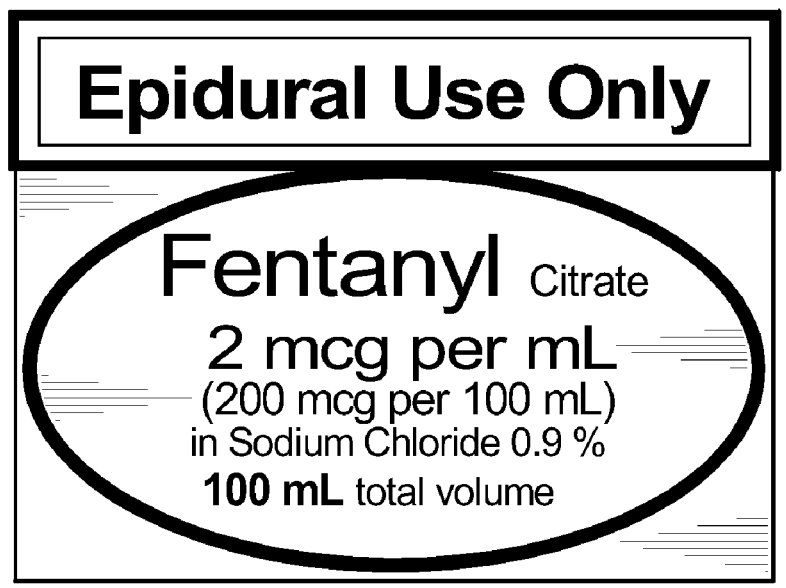
FIG. 18 is a plan view of a drug administration safety device of an embodiment of the present disclosure.
Figure 19:
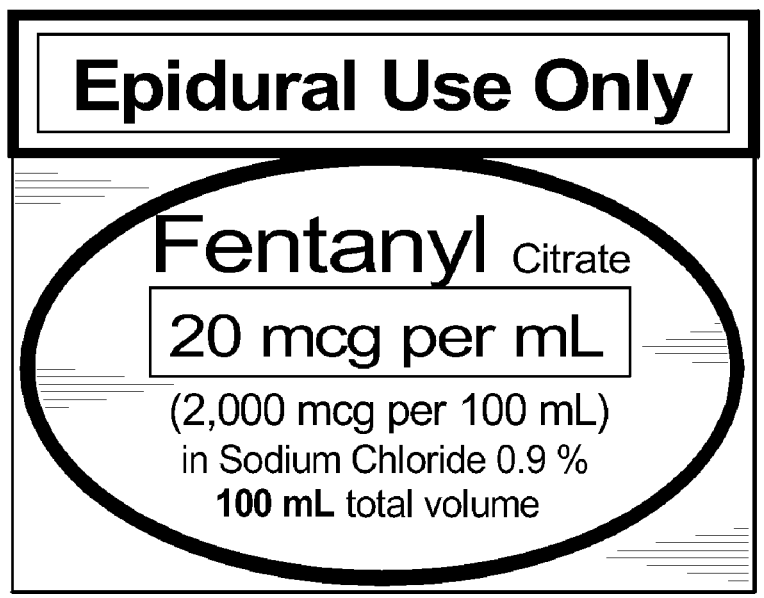
FIG. 19 is a plan view of a drug administration safety device of an embodiment of the present disclosure.

In an embodiment, the drug name and drug dose are situated within two different shapes. For example, as illustrated in FIG. 10, the drug name is situated within an oval shape 332 and the drug concentration is situated in a rectangle shape 334. In alternative embodiments, the shapes are placed adjacent to the label information such as shapes 336a and 336b adjacent to the drug name as illustrated in FIGS. 13, 14 and 15.

Figure 26:
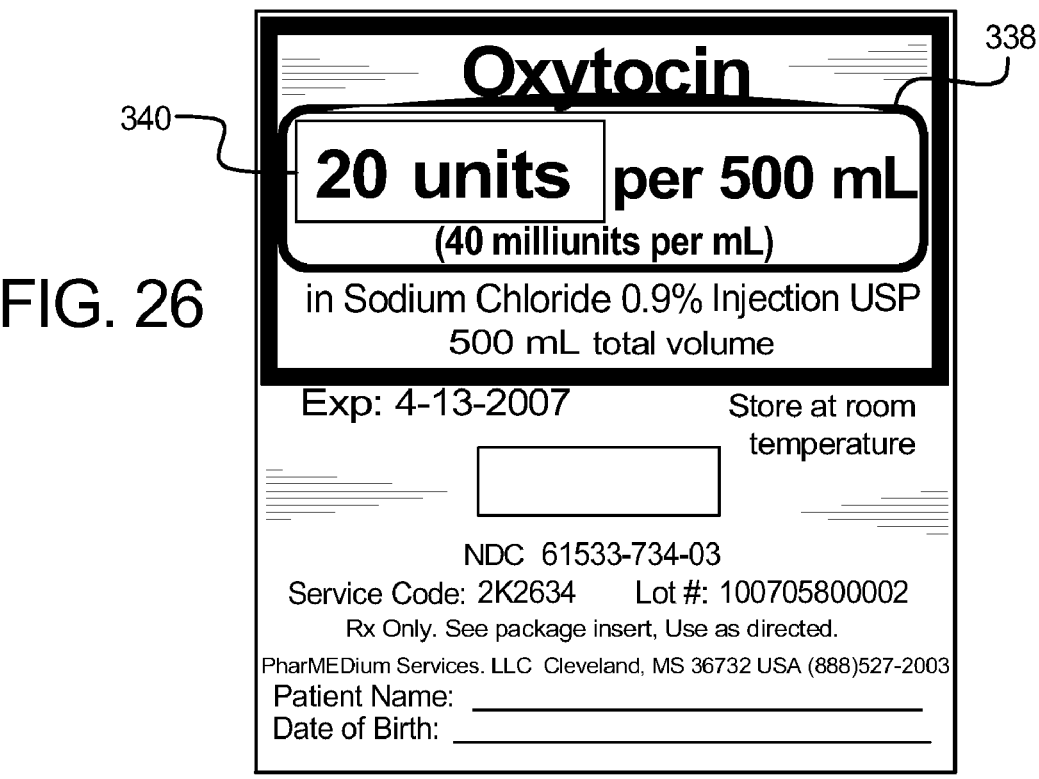
FIG. 26 is a plan view of a drug administration safety device of an embodiment of the present disclosure.
Figure 27:
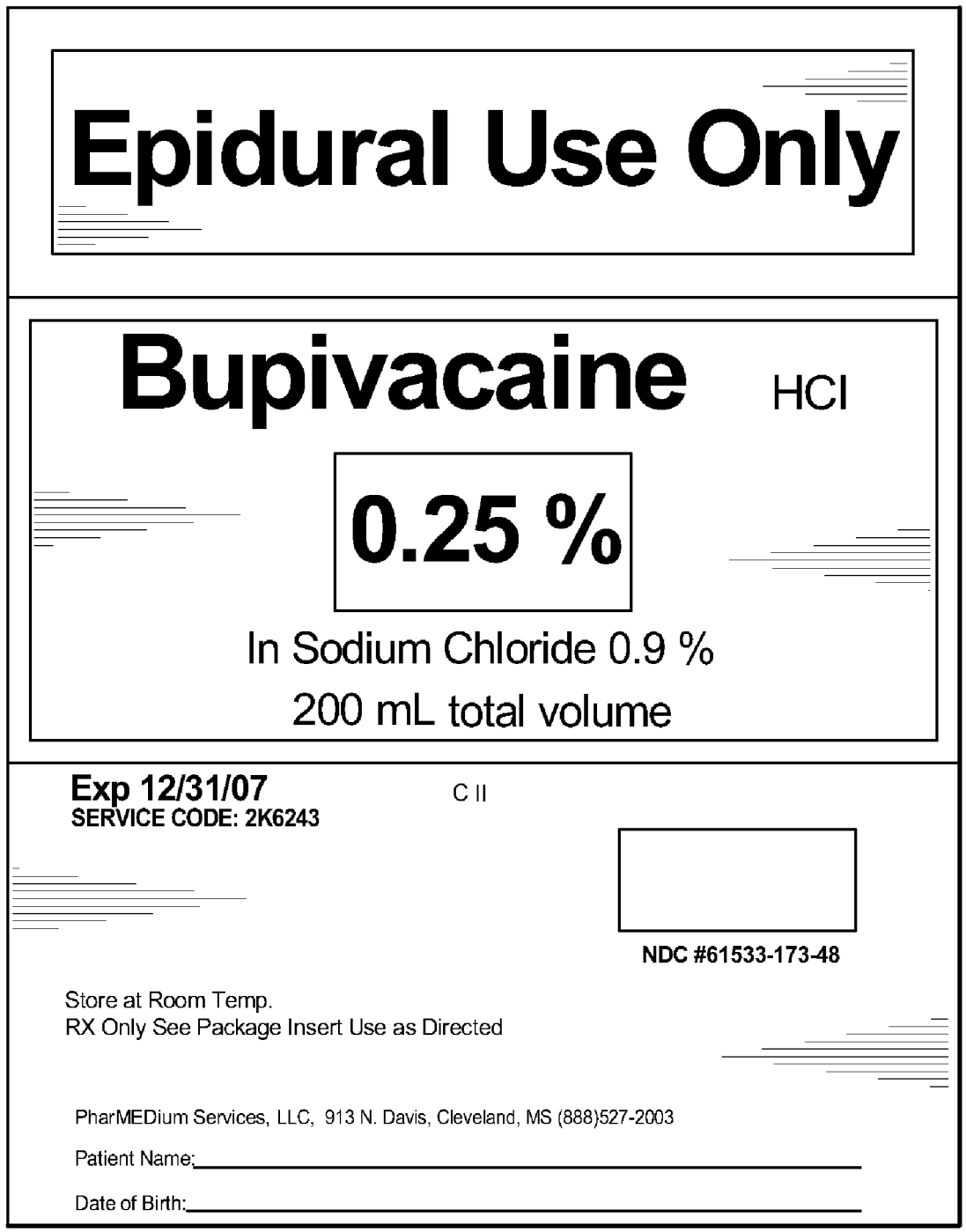
FIG. 27 is a plan view of a drug administration safety device of an embodiment of the present disclosure.
Figure 28:
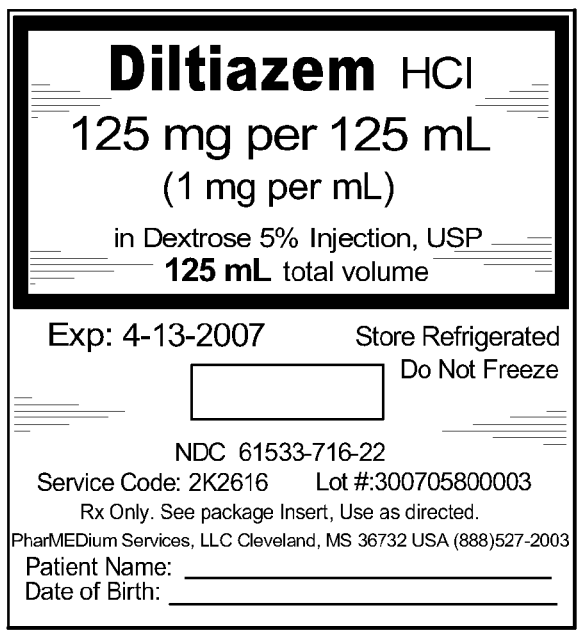
FIG. 28 is a plan view of a drug administration safety device of an embodiment of the present disclosure.
Figure 29:
FIG. 29 is a plan view of a drug administration safety device of an embodiment of the present disclosure.
Figure 30:
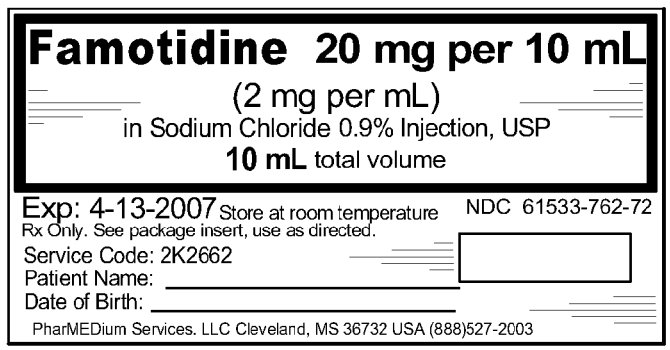
FIG. 30 is a plan view of a drug administration safety device of an embodiment of the present disclosure.
Figure 31:
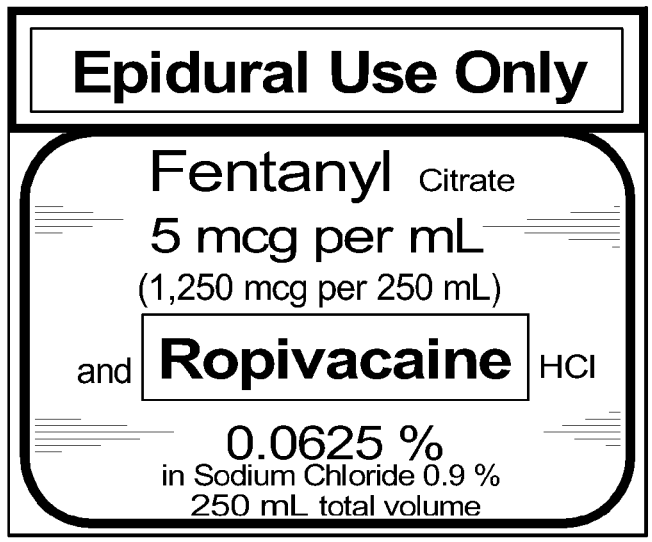
FIG. 31 is a plan view of a drug administration safety device of an embodiment of the present disclosure.
Figure 32:
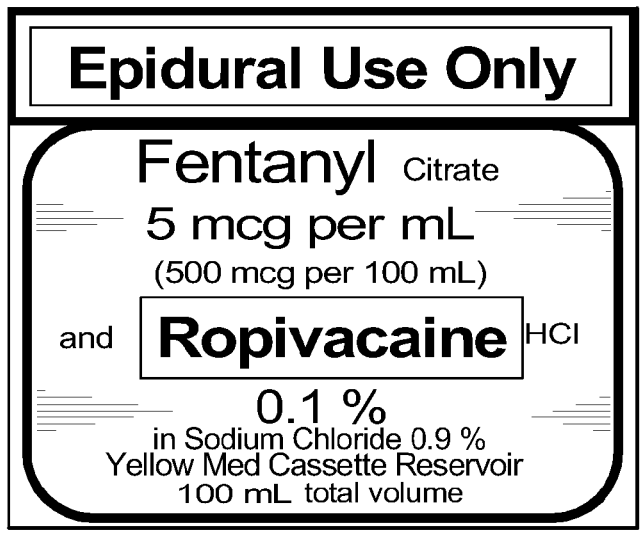
FIG. 32 is a plan view of a drug administration safety device of an embodiment of the present disclosure.
Figure 33:
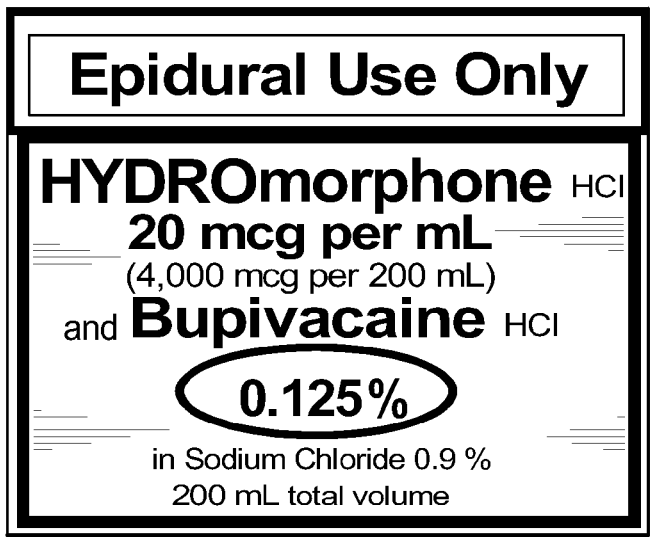
FIG. 33 is a plan view of a drug administration safety device of an embodiment of the present disclosure.
Figure 34:
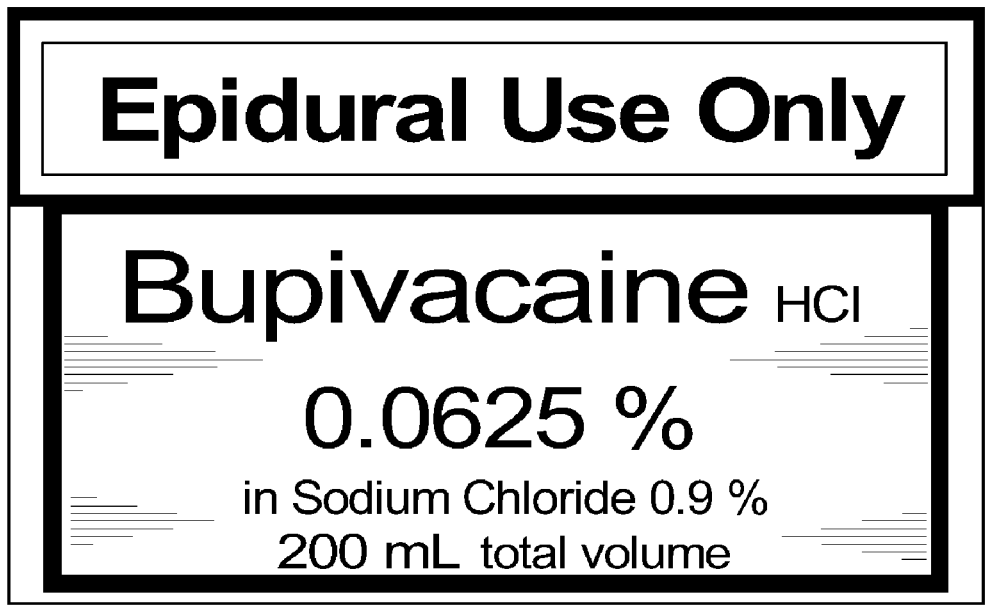
FIG. 34 is a plan view of a drug administration safety device of an embodiment of the present disclosure.
Figure 35:
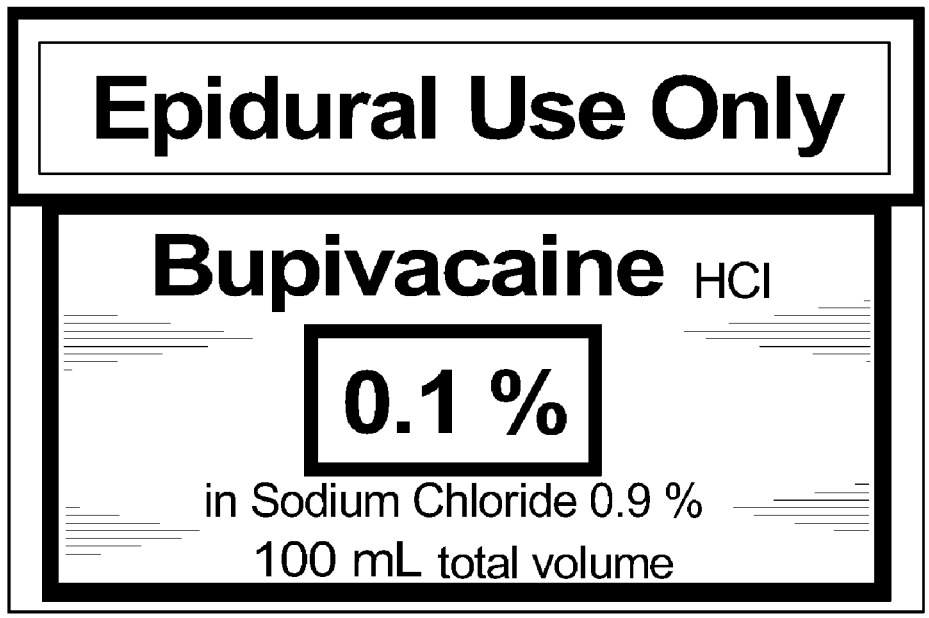
FIG. 35 is a plan view of a drug administration safety device of an embodiment of the present disclosure.
Figure 36:
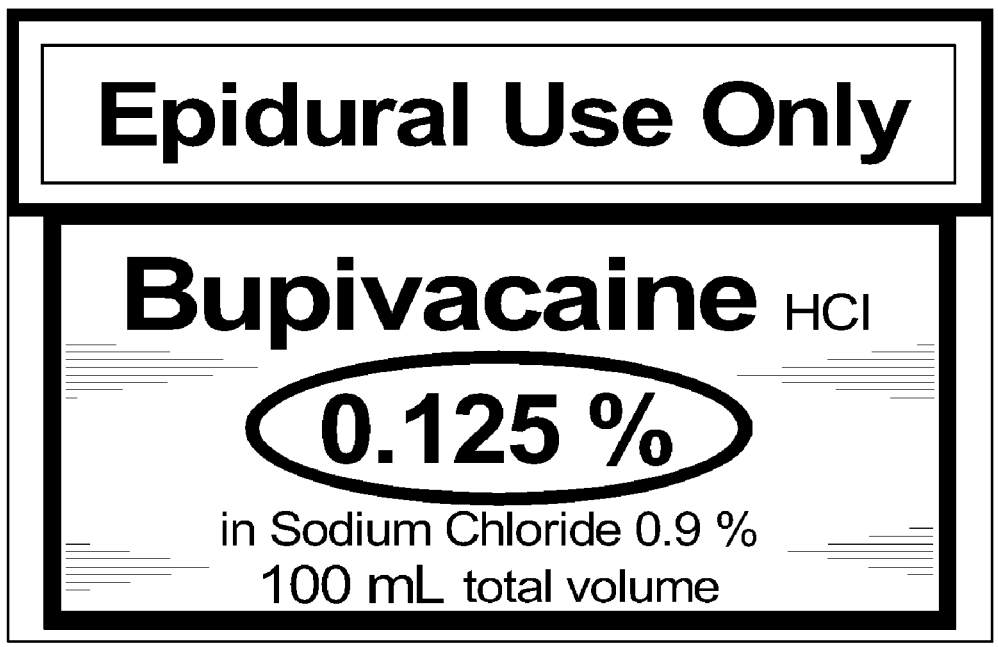
FIG. 36 is a plan view of a drug administration safety device of an embodiment of the present disclosure.
Figure 37:
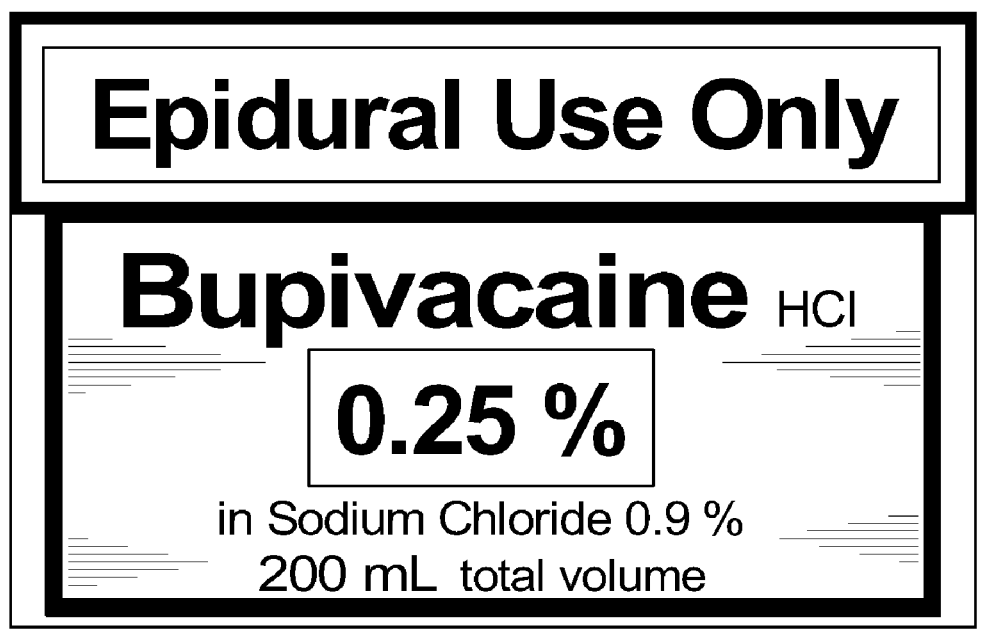
FIG. 37 is a plan view of a drug administration safety device of an embodiment of the present disclosure.
Figure 38:
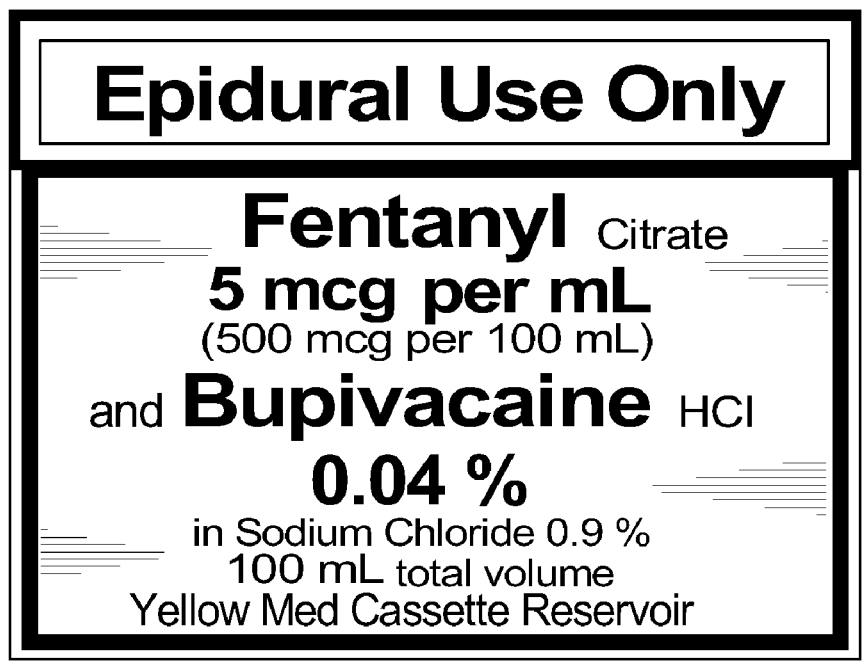
FIG. 38 is a plan view of a drug administration safety device of an embodiment of the present disclosure.
Figure 39:
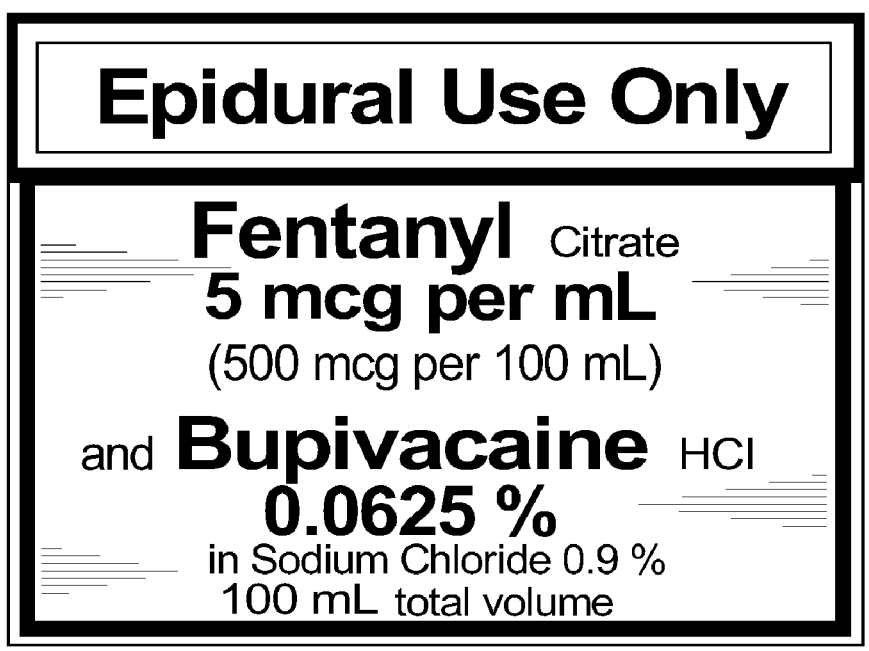
FIG. 39 is a plan view of a drug administration safety device of an embodiment of the present disclosure.
Figure 40:
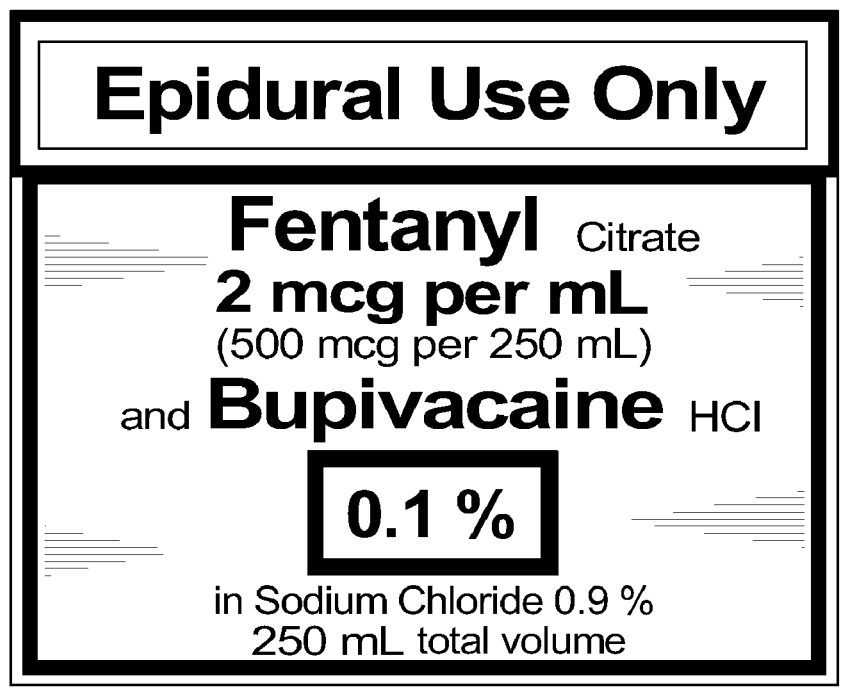
FIG. 40 is a plan view of a drug administration safety device of an embodiment of the present disclosure.
Figure 41:
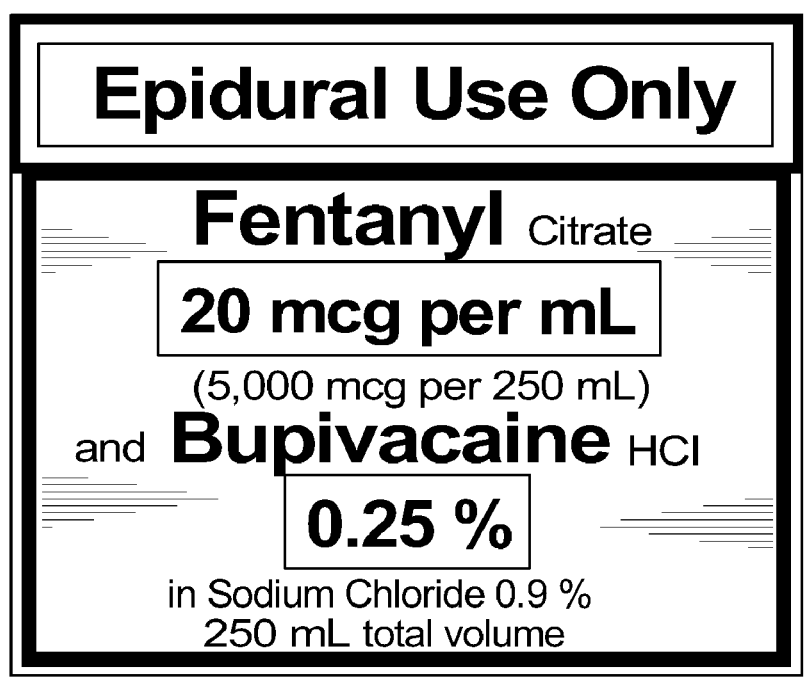
FIG. 41 is a plan view of a drug administration safety device of an embodiment of the present disclosure.
Figure 42:
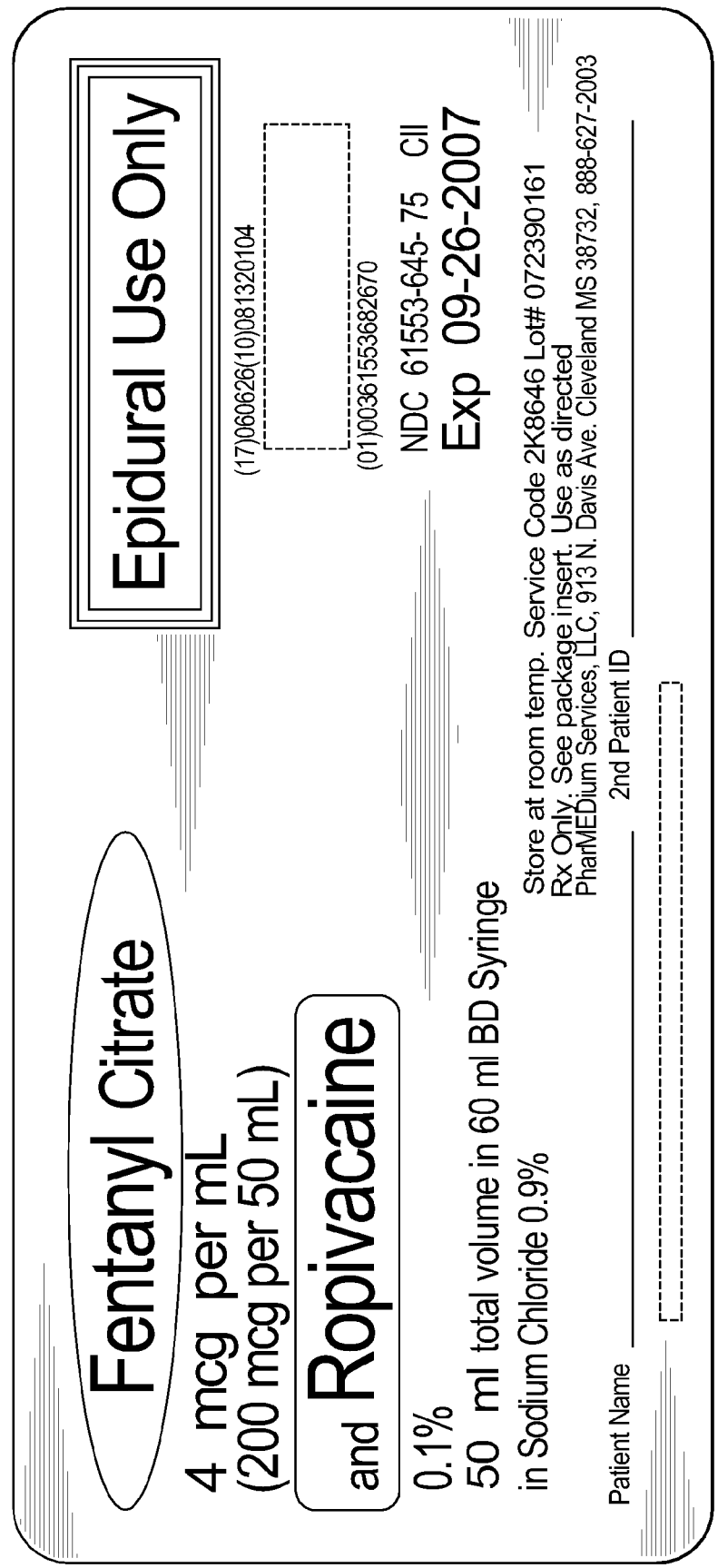
FIG. 42 is a plan view of a drug administration safety device of an embodiment of the present disclosure.
Figure 43:
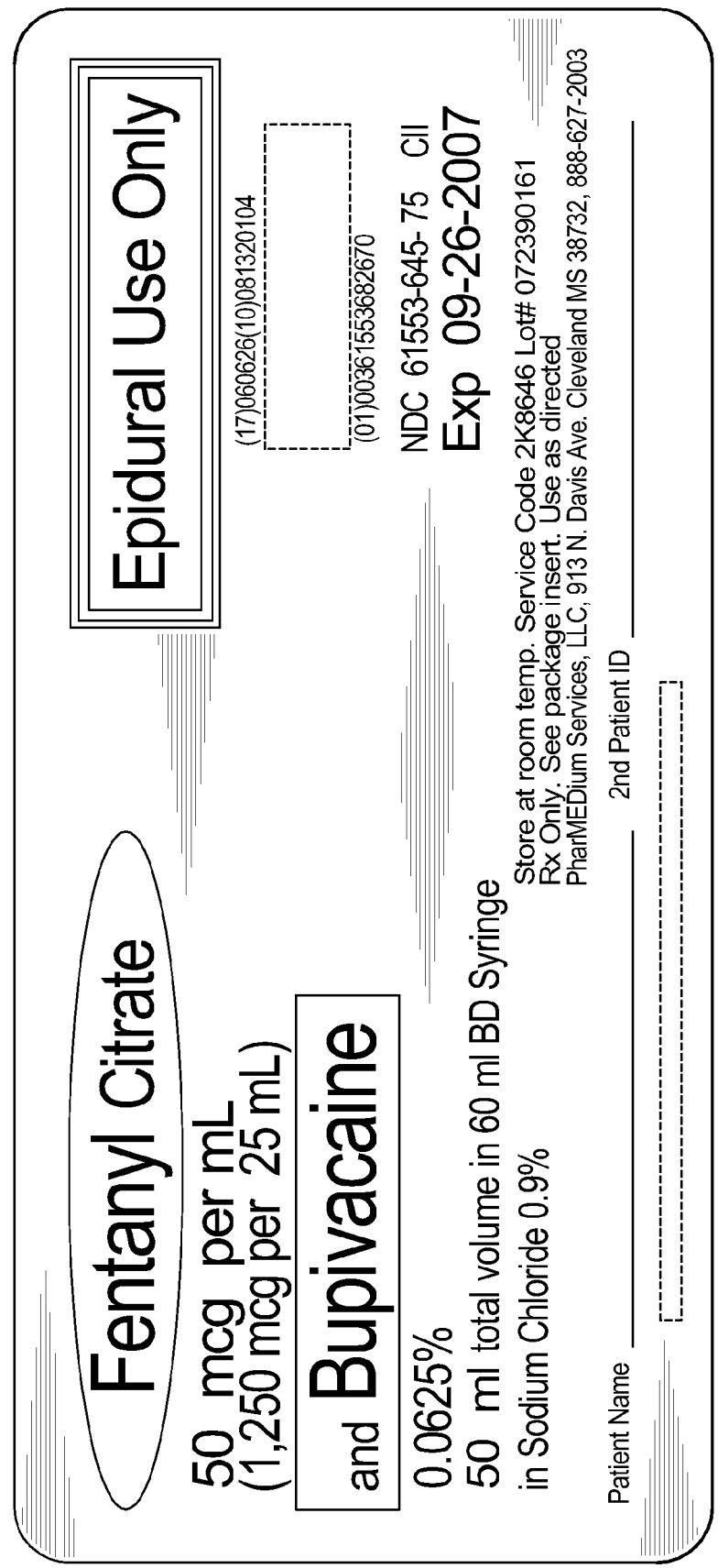
FIG. 43 is a plan view of a drug administration safety device of an embodiment of the present disclosure.

In an embodiment, different portions of label information are situated within one or more shapes. For example, as illustrated in FIG. 26, the concentration of Oxytocin, "20 units per 500 ml" is situated within a rectangle shape 338 having rounded corners. Within the rectangle shape, the dose of "20 units" is further situated inside a second rectangle shape 340. It should be appreciated that the plurality of shapes may be the same or different. Further examples include, but are not limited to, the embodiments illustrated in FIGS. 16, 17, 19, 23 and 24.

In various embodiments, the configuration of the shapes with respect to the label information is different for different doses of the same drug, different variations of the similar drug names or any other distinction in the label that is advantageous and desirable to make.

Figure 9:
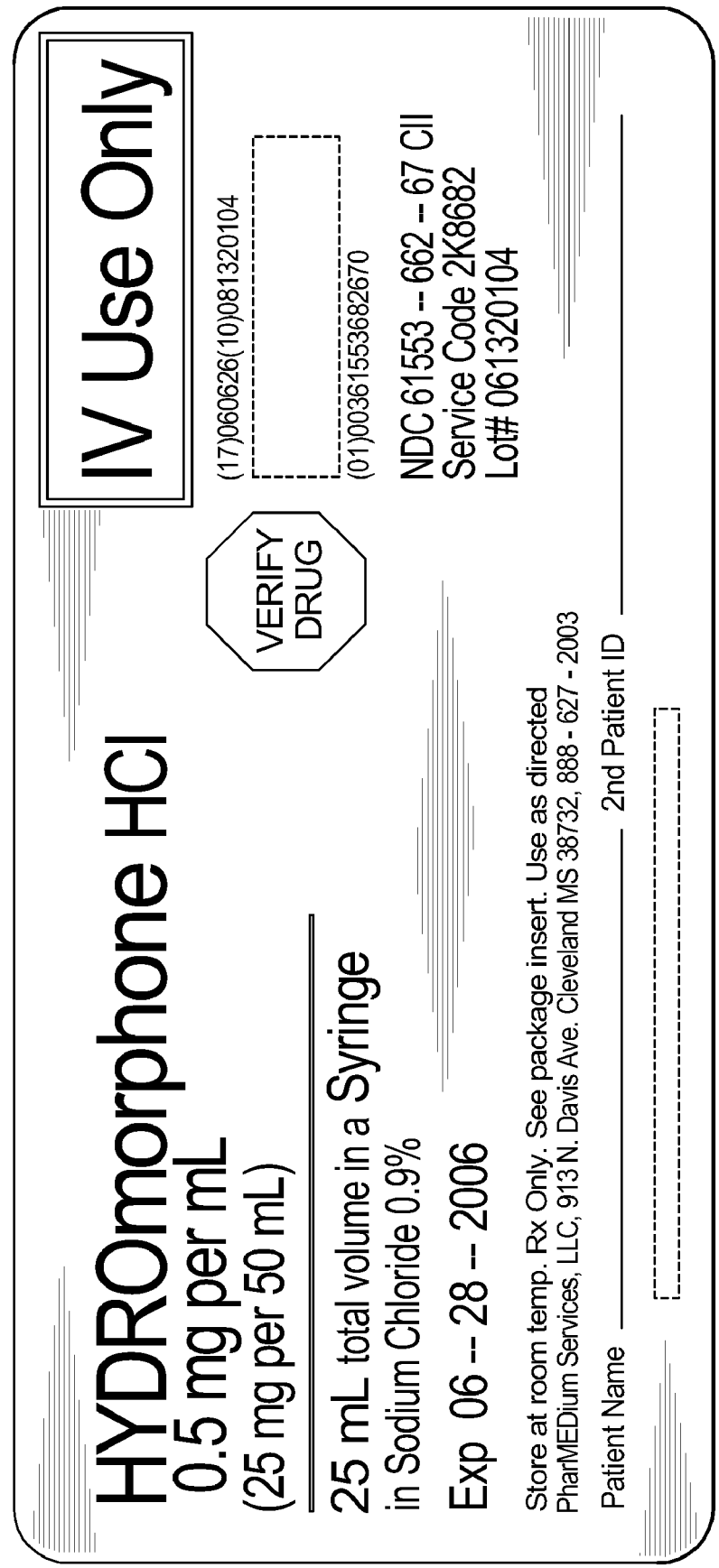
FIG. 9 is a plan view of a drug administration safety device of an embodiment of the present disclosure.

In various embodiments, the label information includes one or more warning statements such as "Verify Drug", "IV Use Only" and "Epidural Use Only". In an embodiment, the warning statement is situated within a shape. For example, as illustrated in FIGS. 8 and 9, the warning statement "Verify Drug" is situated within an octagon or a stop sign 342, indicating that the user should "stop" and read the warning statement. Also, in FIGS. 8 to 15, the warning statement, "IV Use Only", is situated within one or more shapes such as rectangles 344 to highlight the statement. The shapes are filled with a particular shade or color in various embodiments and include an outline of the shape in the same or different shade or color. For example, as illustrated in FIGS. 8 and 9, the stop-sign shape 342 including the warning statement "Verify Drug" may include the color red. Also, in FIGS. 16 to 19, the inner rectangle 344 including the warning statement, "Epidural Use Only", includes the color red, and the outer rectangle 346 includes the color yellow surrounded by a black box.

In an embodiment, the warning statements are positioned on the label to gain the attention of the user such as directly above or adjacent to the drug name. For example, in FIGS. 8 and 9, the stop sign is prominently situated adjacent to the drug name in the middle of the label. In FIGS. 8 to 15, the warning statement "IV Use Only" is prominently situated in the upper right-hand corner of the label so as to be visible in the same vertical plane as the drug name.

In an embodiment, at least one highlighting technique, including shapes, colors, positions and configurations, are uniform for each warning statement. In an embodiment, warning statements, and, in particular, warning statements indicating a particular route of administration, such as "IV Use Only" and "Epidural Use Only" are positioned in the same position on each label for each route of administration. For example, each label illustrated in FIGS. 8 to 15, each with different label information, includes the warning statement, "IV Use Only", situated in the upper right-hand corner of each label. Each label illustrated in FIGS. 16 to 19, each with different label information, includes, the warning statement, "Epidural Use Only", situated at the top of each label.

Figure 20:
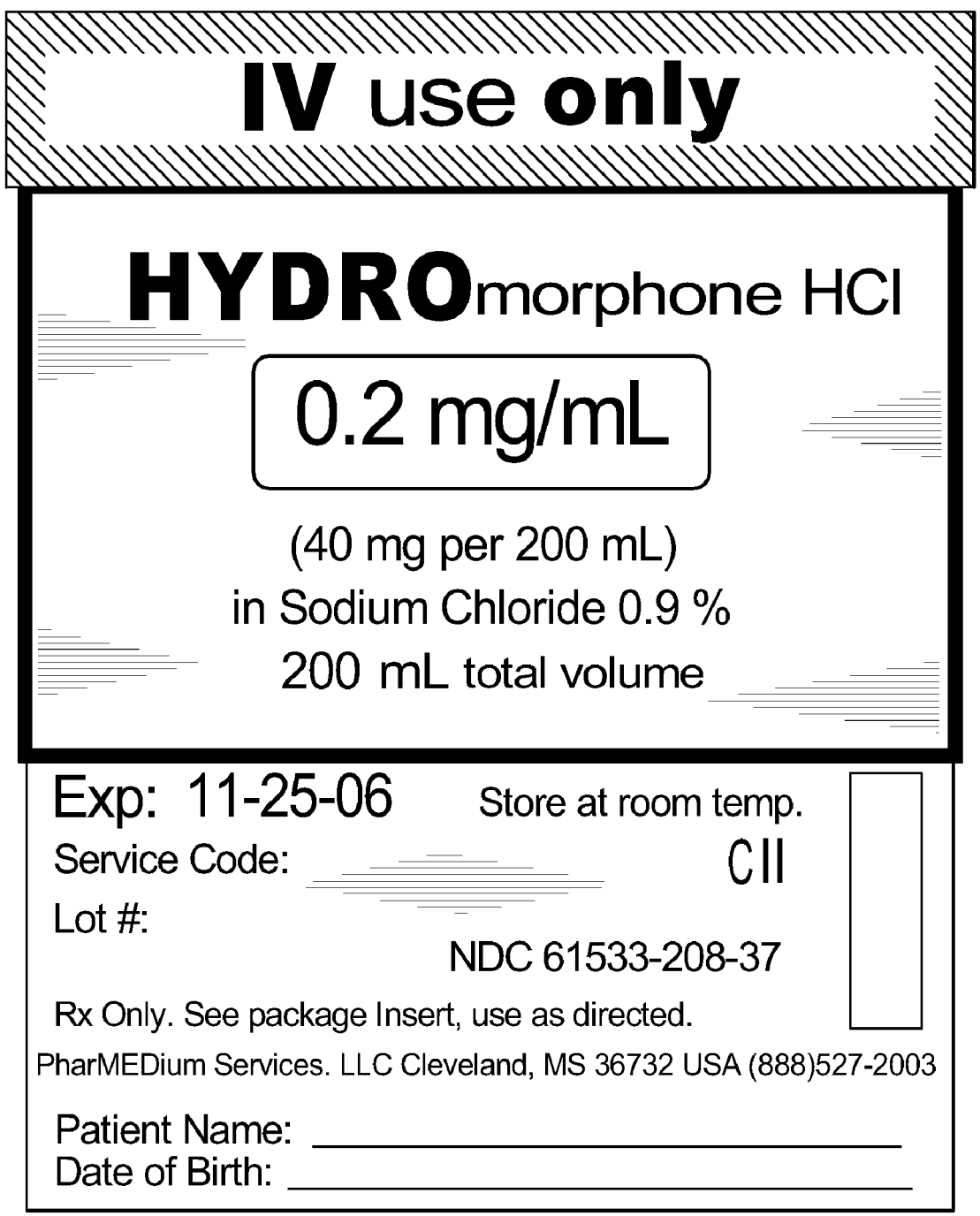
FIG. 20 is a plan view of a drug administration safety device of an embodiment of the present disclosure.
Figure 21:
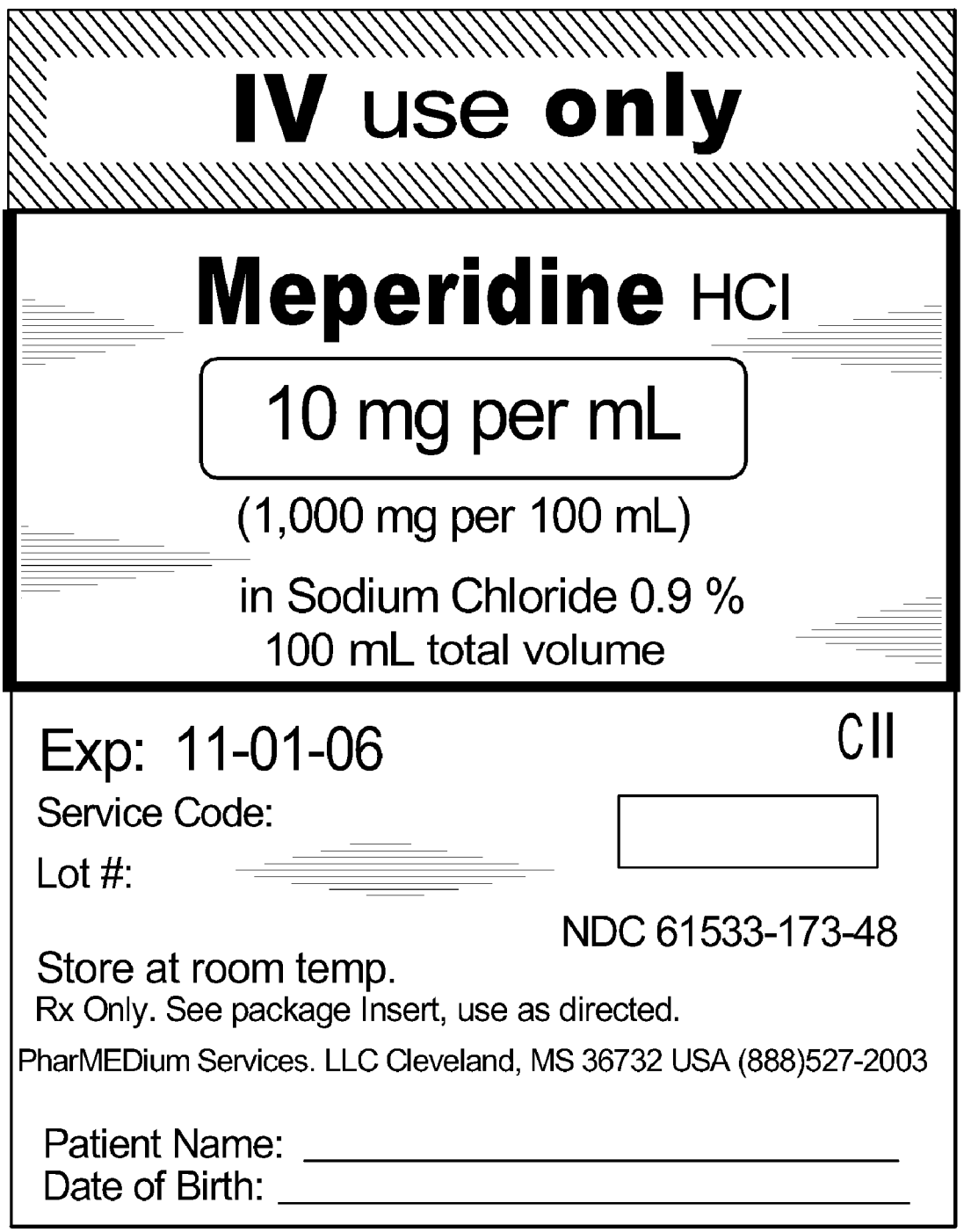
FIG. 21 is a plan view of a drug administration safety device of an embodiment of the present disclosure.
Figure 22:
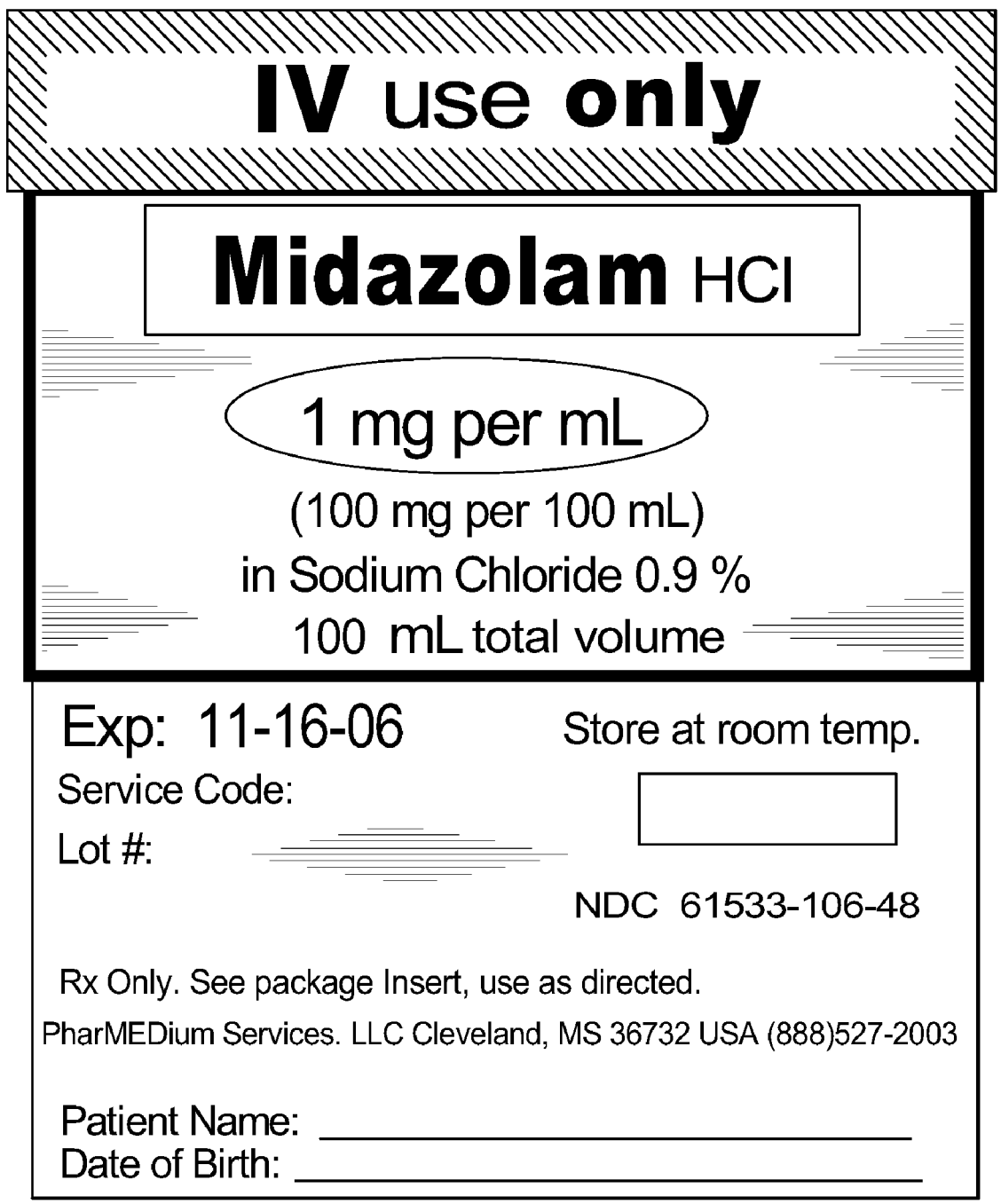
FIG. 22 is a plan view of a drug administration safety device of an embodiment of the present disclosure.
Figure 23:
FIG. 23 is a plan view of a drug administration safety device of an embodiment of the present disclosure.
Figure 24:
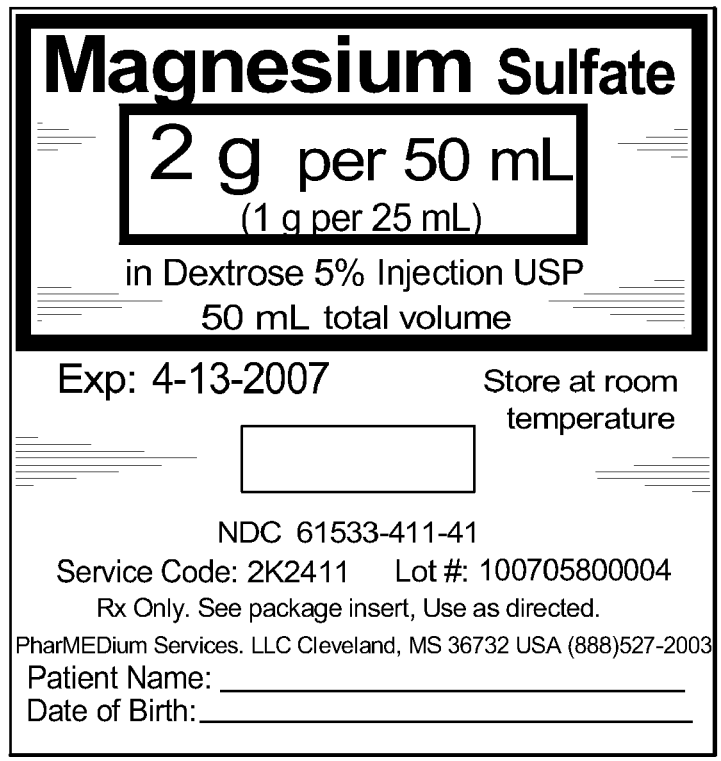
FIG. 24 is a plan view of a drug administration safety device of an embodiment of the present disclosure.
Figure 25:
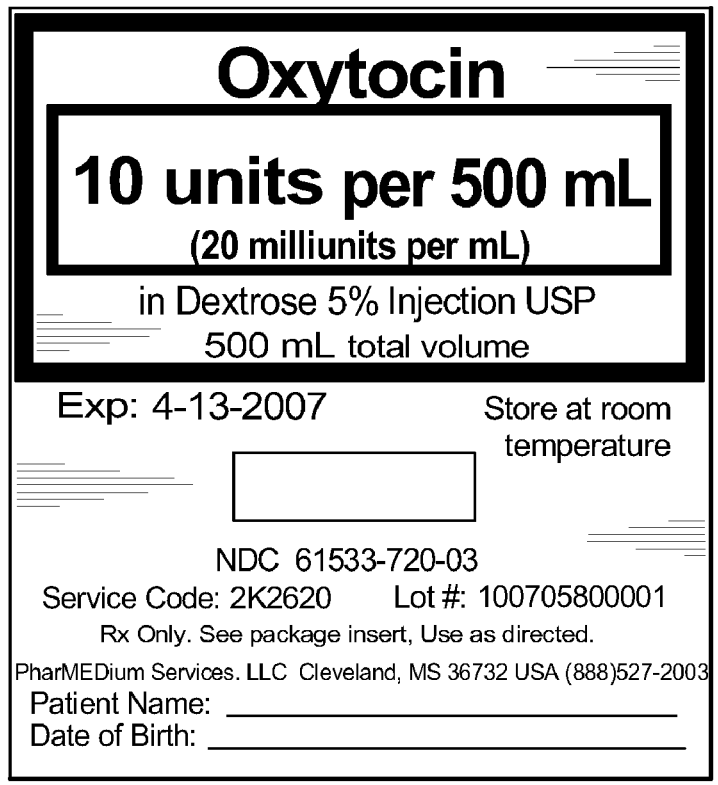
FIG. 25 is a plan view of a drug administration safety device of an embodiment of the present disclosure.

It should be appreciated that the configuration of label information and size and shape of the labels in different embodiments are configured for the particular drug delivery device with which the label is used. In an embodiment, each label for a particular type of drug delivery device includes at least one common shape, color, position and configuration of the label information. For example, in an embodiment, each of the exemplary embodiments illustrated in FIGS. 20 to 22 are configured to be placed on IV PCA (Patient Controlled Analgesia) bags, vials or drug delivery cassettes. In a particular embodiment, the warning statement, "IV use only", appears at the top of each label to be placed on an IV PCA bag, vial or drug delivery cassette. It should also be appreciated that the arrangement of label information may depend on the visibility of certain portions of the label when the drug delivery container is place in a drug delivery device such as a syringe in a pump.

It should be further appreciated that the label elements and information in the illustrated embodiments are not intended to show exact wording, font styles, colors or sizes.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A drug administration safety device comprising:
a single label configured to be attached to a drug container, said drug container including an operating room intravenous syringe configured to contain a drug, said drug having a name including a plurality of letters, said single label including an interior surface and an exterior surface, said single label including:
  (a) a first drug name section in a first orientation, said first drug name section including the letters of the name of the drug, said first drug name section readable when looking at said exterior surface, said letters of the name of the drug in the first drug name section being positioned in said first drug name section such that when the single label is attached to the syringe, said letters of the name of the drug are positioned along a longitudinal section of the syringe and are upright when a plunger of the syringe is positioned below the single label,
  (b) a second drug name section in a second orientation, said second orientation being different from said first orientation, said second drug name section including the letters of the name of the drug, said second drug name section readable when looking at said exterior surface,
  (c) a third drug name section in a third orientation, said third orientation being different from said first orientation, and said third orientation being different from said second orientation, said third drug name section including the letters of the name of the drug, said third drug name section readable when looking at said exterior surface,
  (d) a drug concentration section,
  (e) a variable information section, and
  (f) a graduation viewing section configured to reveal certain portions of the syringe that have information displayed by the syringe or affixed to a surface of the syringe;
  an adhesive on the interior surface of the single label; and
  a backing for holding the single label and protecting the adhesive prior to the application of the single label to the syringe.

2. The drug administration safety device of claim 1, wherein the single label includes a fourth drug name section in a fourth orientation, said fourth orientation being different from the first, second and third orientations, said fourth drug name section including the letters of the name of the drug, said fourth drug name section readable when looking at said exterior surface.

3. The drug administration safety device of claim 1, wherein the graduation viewing section is L-shaped.

4. A method of reducing the risk of error in administration of a drug from a drug container to a patient, said drug having a name including a plurality of letters, said drug container including an operating room intravenous syringe, said method comprising:
  making a single label configured to be attached to the syringe, said single label including an interior surface and an exterior surface, said single label including:
    (a) a first drug name section in a first orientation, said first drug name section including the letters of the name of the drug, said first drug name section readable when looking at said exterior surface, said letters of the name of the drug in the first drug name section being positioned in said first drug name section such that when the single label is attached to the syringe, said letters of the name of the drug are positioned along a longitudinal section of the syringe and are upright when a plunger of the syringe is positioned below the single label,
    (b) a second drug name section in a second orientation, said second orientation being different from said first orientation, said second drug name section including the letters of the name of the drug said second drug name section readable when looking at said exterior surface,
    (c) a third drug name section in a third orientation, said third orientation being different from said first orientation, and said third orientation being different from said second orientation, said third drug name section including the letters of the name of the drug, said third drug name section readable when looking at said exterior surface,
    (d) a drug concentration section,
    (e) a variable information section, and
    (f) a graduation viewing section configured to reveal certain portions of the syringe that have information displayed by the syringe or affixed to a surface of the syringe;
  providing an adhesive on the interior surface of the single label;
  providing a backing for holding the single label and protecting the adhesive prior to the application of the single label to the syringe;
  removing the backing from the single label and attaching the single label without the backing to the syringe; and
  providing the drug container for administration of the drug from the drug container.

5. The method of claim 4, which includes making the single label to include a fourth drug name section in a fourth orientation, said fourth orientation being different from the first, second and third orientations.

6. The method of claim 4, which includes providing the graduation viewing section in an L-shape configuration.

7. A drug container comprising:
  a container, said container including an operating room intravenous syringe;
  a drug contained within the syringe, said drug having a name including a plurality of letters; and
  a single label attached to the syringe, said single label including an interior surface and an exterior surface, said single label including:
    (a) a first drug name section configured in a first orientation on the single label, said first drug name section readable when looking at said exterior surface, said first drug name section including the letters of the name of the drug being positioned in said first drug name section such that said letters of the name of the drug are positioned along a longitudinal section of the syringe and are upright when the syringe is viewed from a first position where a plunger of the syringe is positioned below the single label,
    (b) a second drug name section configured in a second orientation on the single label, said second drug name section readable when looking at said exterior surface, said second drug name section including the letters of the name of the drug being upright when the syringe is viewed from a second position, said second orientation being different from said first orientation, said second position being different from said first position,
    (c) a third drug name section configured in a third orientation on the single label, said third drug name section readable when looking at said exterior surface, said third drug name section including the letters of the name of the drug being upright when the syringe is viewed from a third position, said third orientation being different from said first orientation, said third orientation being different from said second orientation, said third position being different from said first position, and said third position being different from said second position,
(d) a drug concentration section, and
(e) a variable information section.

8. The drug container of claim 7, wherein the single label includes a fourth drug name section in a fourth orientation, said fourth orientation being different from the first, second and third orientations, said fourth drug name section including the letters of the name of the drug being upright when the syringe is viewed from the first position.

9. The drug container of claim 7, which includes an indicator associated with at least one of the first drug name section, the second drug name section, the third drug name section and the drug concentration section.

10. The drug container of claim 9, wherein the indicator is of a form selected from the group consisting of: a shape; a plurality of shapes; a first shape within a second shape, wherein said first shape and said second shape are the same; a first shape within a second shape, wherein said second shape is different from said first shape; a first color within a first shape and a second color within a second shape, wherein said first color and said second color are the same; and a first color within a first shape and a second color within a second shape, wherein said second color is different from said first color.

11. A drug administration safety device comprising:
a single label configured to be attached to an operating room intravenous syringe containing a drug, said drug having a name including a plurality of letters, said drug being of a designated concentration, said single label including an interior surface and an exterior surface, said single label including:
(a) first drug name letters including the letters of said name of the drug contained within the syringe, said first drug name letters readable when looking at said exterior surface, said first drug name letters being upright when the syringe with the single label attached is viewed from a first position, said first drug name letters being of a first size,
(b) second drug name letters including the letters of said name of the drug contained within the syringe, said second drug name letters readable when looking at said exterior surface, said second drug name letters being upright when the syringe with the single label attached is viewed from a second position, said second position and said first position being the same, said second drug name letters being of a second size, said second size being different from said first size,
(c) third drug name letters including the letters of said name of the drug contained within the syringe, said third drug name letters readable when looking at said exterior surface, said third drug name letters being upright when the syringe with the single label attached is viewed from a third position, said third position being different from said first position, said third position being different from said second position, said third drug name letters being of a third size, said third size being different from said first size, and said third size being different from the second size, such that when the single label is attached to the syringe, in one of the first position, the second position, and the third position, a plunger of the syringe is below the drug name letters,
(d) drug concentration letters and numbers indicating the designated concentration of the drug contained within the syringe, and (e) variable information letters and numbers indicating other information relating to the drug contained within the syringe;
an adhesive on the interior surface of the single label; and
a backing for holding the single label and protecting the adhesive prior to the application of the single label to the syringe.

12. The drug administration safety device of claim 11, wherein the single label includes fourth drug name letters including said letters of the name of the drug contained within the syringe, said fourth drug name letters readable when looking at said exterior surface, said fourth drug name letters being upright when the syringe with the single label attached is viewed from a fourth position, said fourth position being different from said first position, said second position and said third position.

13. The drug administration safety device of claim 11, wherein the single label includes a fourth drug name letters including said letters of the name of the drug contained within the syringe, said fourth drug name letters readable when looking at said exterior surface.

14. A drug container comprising:
an operating room intravenous syringe;
a drug contained within the syringe, said drug having a name including a plurality of letters, said drug being of a designated concentration; and
a single label attached to the syringe, said single label including an interior surface and an exterior surface, said single label including:
(a) first drug name letters including the letters of said name of the drug contained within the syringe, said first drug name letters readable when looking at said exterior surface, said first drug name letters being upright when the syringe is viewed from a first position, said first drug name letters being of a first size,
(b) second drug name letters including the letters of said name of the drug contained within the syringe, said second drug name letters readable when looking at said exterior surface, said second drug name letters being upright when the syringe is viewed from a second position, said first position and said second position being the same, said second drug name letters being of a second size, said second size being different from said first size,
(c) third drug name letters including the letters of said name of the drug contained within the syringe, said third drug name letters readable when looking at said exterior surface, said third drug name letters being upright when the syringe is viewed from a third position, said third position being different from said first position, said third position being different from said second position, said third drug name letters being of a third size, said third size being different from said first size, and said third size being different from the second size, such that in one of the first position, the second position, and the third position, a plunger of the syringe is below the drug name letters,
(d) drug concentration letters and numbers indicating the designated concentration of the drug contained within the syringe, and
(e) variable information letters and numbers indicating other information relating to the drug contained within the syringe.

15. The drug container of claim 14, wherein the single label includes fourth drug name letters including said letters of the name of the drug contained within the syringe, said fourth drug name letters readable when looking at said exterior surface, said fourth drug name letters being upright when the syringe is viewed from a fourth position, said fourth position being different from said first position, said second position and said third position.

16. The drug container of claim 14, wherein the single label includes a fourth drug name letters including said letters of the name of the drug contained within the syringe, said fourth drug name letters readable when looking at said exterior surface.

* * * * *